United States Patent
Kubo et al.

(10) Patent No.: US 11,666,915 B2
(45) Date of Patent: Jun. 6, 2023

(54) CELL CLASSIFICATION CHIP

(71) Applicant: TL Genomics Inc., Koganei (JP)

(72) Inventors: Tomohiro Kubo, Koganei (JP); Madoka Ayano, Koganei (JP)

(73) Assignee: TL Genomics Inc., Tokyo (JP)

( * ) Notice: Subject to any disclaimer, the term of this patent is extended or adjusted under 35 U.S.C. 154(b) by 508 days.

(21) Appl. No.: 16/651,027

(22) PCT Filed: Oct. 17, 2018

(86) PCT No.: PCT/JP2018/038728
§ 371 (c)(1),
(2) Date: Mar. 26, 2020

(87) PCT Pub. No.: WO2019/078277
PCT Pub. Date: Apr. 25, 2019

(65) Prior Publication Data
US 2020/0306756 A1    Oct. 1, 2020

(30) Foreign Application Priority Data

Oct. 19, 2017 (JP) .............................. JP2017-202907

(51) Int. Cl.
*B01L 3/00* (2006.01)
*G01N 15/10* (2006.01)
(Continued)

(52) U.S. Cl.
CPC ...... *B01L 3/502761* (2013.01); *C12Q 1/6841* (2013.01); *G01N 15/1056* (2013.01);
(Continued)

(58) Field of Classification Search
CPC ....... B01L 3/502761; B01L 2200/0652; B01L 2300/0874; C12Q 1/6841; G01N 15/1056;
(Continued)

(56) References Cited

U.S. PATENT DOCUMENTS

| 5,731,156 A | 3/1998 | Golbus |
| 5,962,234 A | 10/1999 | Golbus |
| 2012/0301867 A1 | 11/2012 | Kumo et al. |

FOREIGN PATENT DOCUMENTS

| JP | 2005-205387 A | 8/2005 |
| JP | 2007-175684 A | 7/2007 |

(Continued)

OTHER PUBLICATIONS

Kubo, JP 2018-102242 English Machine Translation of Description, obtained on Aug. 1, 2022. (Year: 2022).*

(Continued)

*Primary Examiner* — Christine T Mui
(74) *Attorney, Agent, or Firm* — Maier & Maier, PLLC

(57) ABSTRACT

A chip includes a micro-channel unit for hydraulically classifying cells in a blood sample. In a micro-channel unit, liquid flowing from a sub channel into a main channel pushes cells flowing in the main channel toward a side thereof on which a removal channel and a collection channel are disposed. Fluid containing non-nucleated RBCs among the pushed cells enters the removal channel, so that the non-nucleated RBCs are removed from a blood sample. A plurality of micro-channel units having the same patterns as each other are repeatedly stacked in a height direction. Inlets of the main channels, inlets of the sub channels, outlets of the removal channels, outlets of the collection channels, and outlets of the main channels, which are provided in the micro-channel units, are connected to respective pillar channels penetrating each of layers in a traversing manner.

14 Claims, 15 Drawing Sheets

(51) Int. Cl.
*C12Q 1/6841* (2018.01)
*G01N 33/58* (2006.01)
*C12Q 1/68* (2018.01)
*G01N 15/00* (2006.01)

(52) U.S. Cl.
CPC .... *G01N 33/582* (2013.01); *B01L 2200/0652* (2013.01); *B01L 2300/0874* (2013.01); *G01N 2015/008* (2013.01); *G01N 2015/0073* (2013.01); *G01N 2015/1081* (2013.01)

(58) Field of Classification Search
CPC ......... G01N 33/582; G01N 2015/0073; G01N 2015/008; G01N 2015/1081
USPC ....................................................... 435/6.11
See application file for complete search history.

(56) References Cited

FOREIGN PATENT DOCUMENTS

| | | | |
|---|---|---|---|
| JP | 2007-530629 A | 11/2007 | |
| JP | 4091123 B2 | 5/2008 | |
| JP | 2009-511001 A | 3/2009 | |
| JP | 5308834 B2 | 10/2013 | |
| JP | 5311356 B2 | 10/2013 | |
| JP | 5857537 B2 | 2/2016 | |
| JP | 2018-102242 * | 7/2018 | ............... C12Q 1/68 |
| KR | 1020170062041 A | 6/2017 | |
| WO | 2005/100401 A2 | 10/2005 | |
| WO | 2007/035498 A2 | 3/2007 | |

OTHER PUBLICATIONS

JP 2018-102242 English Machine Translation of Description. Obtained from espacent, pp. 1-88. 2022. (Year: 2022).*
International Search Report dated Feb. 5, 2019 in corresponding International Application No. PCT/JP2018/038728; 5 pages.
Taizan Kamide, Nagayoshi Umehara, Haruhiko Sago, "New Trials For Efficient Erythroblast Isolation From Maternal Blood", Sei-i-Kai, Tokyo Jikeikai Medical Journal, 2015, 130: 11-7, 11 pgs.
Office Action dated Sep. 13, 2022, in corresponding Indian Application No. 202017017381, 5 pages.
Matsuda et al., "Blood Cell Classification Utilizing Hydrodynamic Filtration", Electronics and Communications in Japan, vol. 94, No. 1, 2011, 6 pages.
Sajeesh et al., "Microfluidic device with focusing and spacing control for resistance based sorting of droplets and cells", Lab on a Chip, Jul. 21, 2015, Royal Society of Chemistry, www.rsc.org/loc, DOI:10.1039/C5LC00598A., 14 pages.

* cited by examiner

CELL CLASSIFICATION CHIP

FIELD

The present invention relates to a cell classification chip for concentrating rare target cells in a blood sample.

BACKGROUND

To explain a method for concentrating rare target cells in a blood sample and separating them from the blood sample according to background art, noninvasive prenatal genetic testing (NIPT) is described as an example of such a method. The NIPT is one of the methods for testing a fetal chromosome. This testing method is characterized in that it does not involve centesis in an amnion. Since the burden on a mother and a fetus imposed in the NIPT is small as compared to that in the method involving centesis in the amnion, the NIPT has been rapidly spreading throughout the world.

As an aspect of the NIPT, a technique for diagnosing a fetal chromosome is under development. Therefore, it has been attempted to separate fetal-derived nucleated red blood cells (NRBCs) (hereinafter also simply called NRBCs) from maternal blood by using a micro-channel chip in order to obtain a chromosome. The NRBCs are a type of rare target cells.

Patent Literature 1 discloses a concentration method using a micro-channel chip. In this method, blood is made to pass through a slit having a width of 1 μm, so that red blood cells (RBCs) and white blood cells (WBCs) are made to pass through the slit. The NRBCs are retained before the slit. The retained NRBCs are removed from the chip.

Patent Literature 2 discloses a method in which after NRBCs are concentrated by using a device equipped with a channel for deterministically guiding particles based on their hydraulic size, their magnetic property is changed and they are separated by applying a magnetic field thereto, so that the NRBCs are further concentrated (paragraphs [0083] and [0202]). Note that the term "hydraulic size" means the effective size of a particle when it interacts with a flow, a barrier structure (e.g., a column), or other particles (paragraph [0041]).

Further, in Patent Literature 2, for a group of blood cells in which NRBCs are concentrated, the NRBCs are identified by observing their cell nuclei by a fluorescence in situ hybridization (FISH) method.

Patent Literature 1: Japanese Patent No. 5311356
Patent Literature 2: Japanese Unexamined Patent Application Publication No. 2009-511001
Patent Literature 3: Japanese Unexamined Patent Application Publication No. 2005-205387
Patent Literature 4: Japanese Unexamined Patent Application Publication No. 2007-175684
Patent Literature 5: Japanese Patent No. 4091123
Patent Literature 6: Published Japanese Translation of PCT International Publication for Patent Application, No. 2007-530629
Patent Literature 7: Japanese Patent No. 5857537
Patent Literature 8: Japanese Patent No. 5308834
Non-patent Literature 1: Taizan KAMIDE, Nagayoshi UMEHARA, Haruhiko SAGO, "New Trials For Efficient Erythroblast Isolation From Maternal Blood", Sei-i-Kai, Tokyo Jikeikai Medical Journal, 2015, 130(1): 11-17

SUMMARY

In Patent Literature 1, the volume of a sample liquid that can be processed by the chip is no larger than the order of "μl". Therefore, it is considered that prior to the concentration process using the chip, a separation process by a density gradient centrifugation method or the like preferably should be performed (the same literature, paragraph [0040]). It is considered that the chip disclosed in Patent Literature 1 is not suitable for processing whole blood containing a large number of WBCs and non-nucleated RBCs.

In Patent Literature 2, NRBCs are concentrated based on the hydraulic size by using the device. The concentration based on the hydraulic size can be applied to whole blood. However, it requires a further concentration using the magnetic property.

When a prenatal diagnosis is performed, needless to say, the amount of a maternal blood sample that can be collected from a subject is limited. Further, it is obstetrically obvious that each pregnant woman, i.e., each subject of a prenatal diagnosis has only a limited period during which the diagnosis can be performed. Further, the number of NRBCs derived from a fetus in blood is extremely small. Such rare cells cannot be sufficiently concentrated by using the conventional concentration methods. This problem is not limited to the NIPT, but similar problems also occur when it is desired to concentrate rare target cells in whole blood. A concentration of fetal-derived NRBCs in the NIPT is its typical example.

An object of the present invention is to provide means for improving efficiency in a technique in which rare target cells in whole blood are concentrated by using a micro-channel chip for cell classification.

<1>

A chip including a micro-channel unit for hydraulically classifying cells in a blood sample, in which the micro-channel unit includes a pattern in which a main channel through which the blood sample flows, a sub channel connected to a side of the main channel, a removal channel connected, downstream from the sub channel, to a side of the main channel opposite to the side thereof to which the sub channel is connected, and a collection channel connected, downstream from the removal channel, to the side of the main channel opposite to the side thereof to which the sub channel is connected are two-dimensionally extended, liquid flowing from the sub channel into the main channel pushes cells flowing in the main channel toward the side thereof on which the removal channel and the collection channel are disposed, fluid containing non-nucleated RBCs among the pushed cells enters the removal channel, so that the non-nucleated RBCs are removed from the blood sample, fluid containing target cells among the remaining cells from which the non-nucleated RBCs have been removed enters the collection channel, so that the target cells are acquired from the blood sample, a volume of flow per unit time, in each collection channel, on a cross section of a connecting part between the main channel and that collection channel is larger than a volume of flow per unit time, in each removal channel, on a cross section of a connecting part between the main channel and that removal channel, a plurality of micro-channel units having the same patterns as each other are repeatedly stacked in a height direction, and inlets of the main channels, inlets of the sub channels, outlets of the removal channels, outlets of the collection channels, and outlets of the main channels, which are provided in the micro-channel units, are connected to respective pillar channels penetrating each layer in a traversing manner so that they are separately put together by the respective pillar channels.
<2>
The chip described in the Item <1>, in which one micro-channel unit is provided in each of the layers.
<3>
The chip described in the Item <2>, in which orientations and positions of the patterns of the micro-channel units of all the layers are aligned with each other in a planer view of the chip.
<4>
The chip described in the Item <3>, in which
the pillar channels to which the inlets of the main channels and the sub channels are respectively connected have openings on a top surface of the chip, and
the pillar channels to which the outlets of the removal channels and the collection channels are respectively connected have openings on a bottom surface of the chip,
so that the blood sample passes through the chip from the top surface of the chip to the bottom surface thereof.
<5>
The chip described in the Item <4>, in which the layers, in which the micro-channel units are provided, are successively stacked at regular intervals.
<6>
The chip described in the Item <1>, in which
an inscribed diameter of the removal channel at the connecting part between the main channel and the removal channel is 4 to 19 μm, and
an inscribed diameter of the collection channel at the connecting part between the main channel and the collection channel is 20 to 30 μm.
<7>
The chip described in the Item <1>, in which in the micro-channel unit, a cross-sectional area of at least one of the collection channel and the removal channel becomes larger toward downstream of it.
<8>
A use of the chip described in the Item <4> for acquiring a fraction in which the target cells are concentrated in terms of the number of cells by fractionating the blood sample, in which
the blood sample is non-treated whole blood itself or one in which the target cells are not concentrated in terms of the number of cells as compared to the whole blood.
<9>
The use described in the Item <8>, in which a volume of inflow of the blood sample to the pillar channel to which the main channel is connected is 8 to 25 μl/min.
<10>
The use described in the Item <9>, in which a volume of inflow per unit time of the liquid to the pillar channel to which the sub channel is connected is 1 to 2 times a volume of inflow per unit time of the blood sample to the pillar channel to which the main channel is connected.
<11>
The use described in the Item <8>, in which while the blood sample is being injected into the chip, the blood sample that is held before being injected into the chip is stirred, and the stirred blood sample is successively injected into the chip.
<12>
The use described in the Item <8>, in which the blood sample is whole blood of maternal blood or one that is obtained by simply diluting the whole blood, and the target cells are fetal-derived NRBCs.
<13>
A method including:
acquiring a fraction A in which NRBCs are concentrated based on a use of the chip described in the Item <12>:
acquiring a fraction B by specifically labeling WBCs and nucleic acids in the fraction A and sorting out labeled blood cells in the fraction A by cell sorting, in which blood cells labeled with a label specific to the WBCs have been removed from the fraction B and blood cells labeled with a label specific to the nucleic acids have been concentrated in the fraction B; and
acquiring data to be used for a diagnosis in noninvasive prenatal genetic testing by analyzing a chromosome contained in the blood cells in the fraction B.
<14>
The method described in the Item <13>, in which the analysis of the chromosome is an analysis according to a fluorescence in situ hybridization method, a next generation sequencing method, or a microarray method.

According to the present invention, it is possible to provide means for improving efficiency in a technique in which rare target cells in whole blood are concentrated by using a micro-channel chip for cell classification.

DETAILED DESCRIPTION

Figure 1:
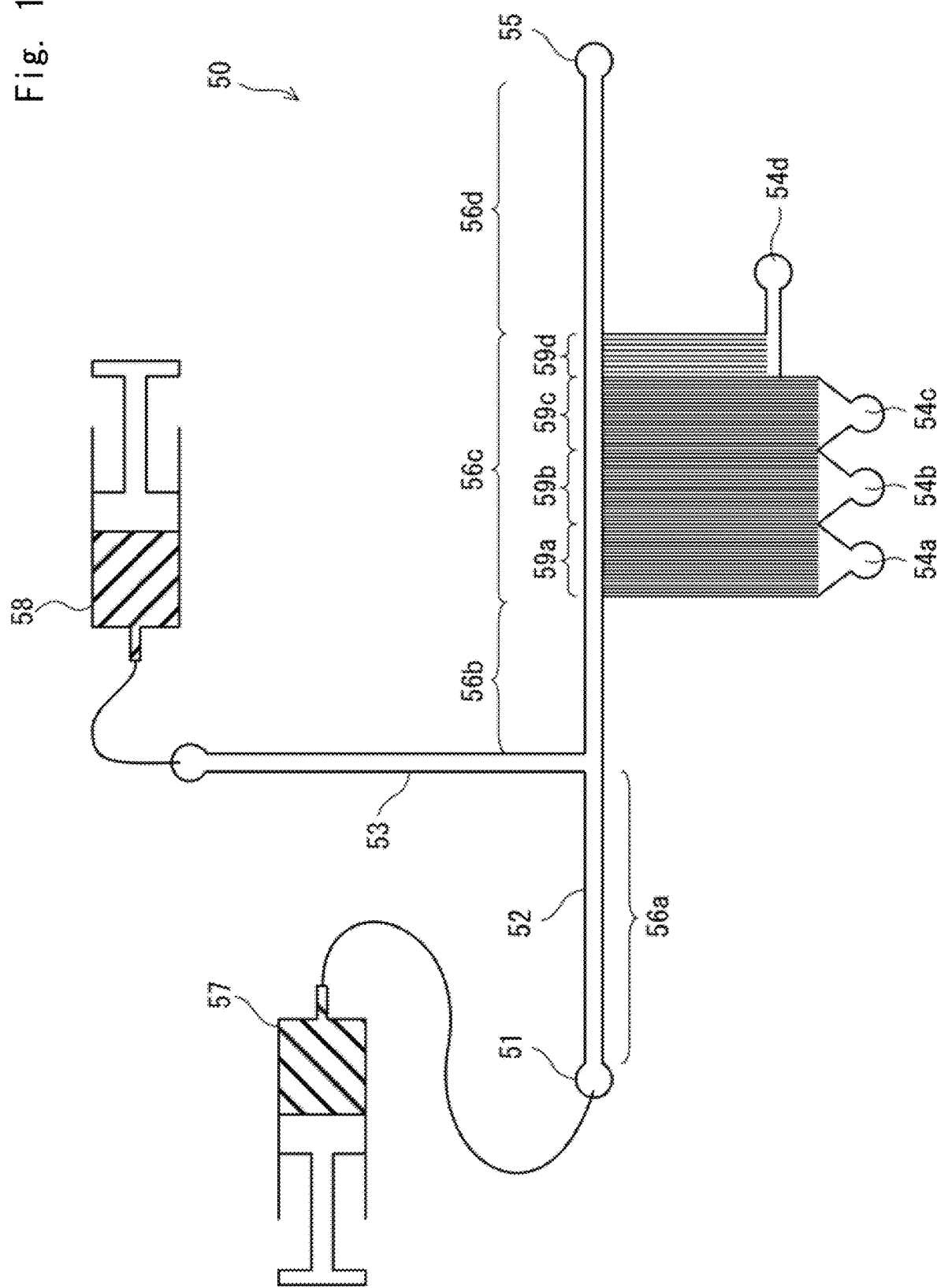
FIG. 1 is a planer view of a blood-cell separation chip.

In this embodiment, details of a chip including micro-channel units for hydraulically classifying cells in a blood sample are described, in particular, from the viewpoint of its use. Specifically, they are described by describing a process for concentrating target cells in a blood sample by using such a chip as an example. The target cells are a cell strain to be concentrated. In this specification, the term "concentration" means to increase the frequency of cells in terms of the number of cells. In this embodiment, NRBCs, i.e., the so-called erythroblasts are concentrated as an example of the target cells. Note that the blood sample may be non-treated whole blood itself. The blood sample may be a sample in which NRBCs are not concentrated in terms of the number of cells as compared to whole blood, i.e., may be the so-called un-filtered/un-concentrated sample. The blood sample contains at least non-nucleated RBCs, i.e., mature RBCs and target cells.

[Collecting Blood]

In this embodiment, the starting material is a maternal blood sample of a human pregnant woman. For pregnant women, the fetal age after menstruation is preferably from 10 weeks to 33 weeks. The fetal age after menstruation is expressed by the number of completed days or completed weeks while defining the first day of the last menstrual period as the first day. The fetal age after menstruation may be calculated by adding two weeks to the fetal age after fertilization. Examples of the blood sample include maternal blood or one obtained by diluting maternal blood. The chip according to this embodiment and the use thereof can be applied to substances other than the maternal blood. In the following description of the embodiment, maternal blood may be replaced with other blood samples and the technical matters thereof may be interpreted accordingly.

The maternal blood sample may be non-treated maternal blood itself. The maternal blood sample may be maternal blood that has been changed by performing some type of chemical or physical process on the original maternal blood so that the changed maternal blood becomes suitable for preservation and efficiency of subsequent processes. Such processes include, for example, adding a preservative such as an apoptosis inhibitor, adjusting a temperature, adding a reagent to prevent precipitation of blood cells, and protecting blood cells from physical damage caused by shaking by using an air cushion. However, the processes are not limited to these examples.

In this embodiment, the maternal blood means blood collected from a pregnant woman. The maternal blood can be collected from a pregnant woman by an ordinary medical method. NRBCs in the collected maternal blood may be concentrated immediately. Further, NRBCs may be concentrated after the maternal blood is transported from a place where the blood is collected to where the blood is concentrated. A desired preservative process may be performed on the maternal blood.

An amount of necessary maternal blood is considered as follows. In general, it is known that about $3\times10^{10}$ blood cells are contained in 10 ml of maternal blood. Further, it is known that about 36 to 2168 NRBCs are contained in maternal blood having the same volume (Non-patent Literature 1).

In view of the above-described ratio of NRBCs, an amount of maternal blood used as a starting material may be 0.01 to 100 ml. The amount of the maternal blood may be 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 30, 40, 50, 60, 70, 80 or 90 ml.

[Fetal-Derived Cell]

In this embodiment, an object is to acquire concentrated fetal-derived cells. As an example of the fetal-derived cells, NRBCs contained in maternal blood are described hereinafter.

In this embodiment, blood cells mean cells in blood. Blood contains blood cells and blood plasma. According to one theory, it is considered that RBCs account for the greater part of human blood cells. Further, WBCs and blood platelets are also included in the blood cells. Maternal blood contains NRBCs derived from a fetus.

In this embodiment, the NRBCs are erythroblasts and preferably erythroblasts that have lost their cell-division ability. RBCs are generated as hematopoietic stem cells differentiate and mature. Through the process of differentiation and maturation, starting from the hematopoietic stem cells, myeloid progenitor cells, RBCs/megakaryocyte precursor cells, prophase erythroid precursor cells (BFU-E), anaphase erythroid precursor cells (CFU-E), proerythroblasts, basophilic erythroblasts, polychromatic erythroblasts, orthochromatic erythroblasts, reticulocytes, and erythrocytes appear one after another.

The erythroblasts include proerythroblasts, basophilic erythroblasts, polychromatic erythroblasts, and orthochromatic erythroblasts. Nucleuses are lost from blood cells during the process in which orthochromatic erythroblasts differentiate into reticulocytes. In general, orthochromatic erythroblasts have already lost their cell-division ability.

NRBCs are usually present in bone marrow. However, as described above, a very small number of NRBCs are found in blood. Further, a very small number of NRBCs of maternal origin and NRBCs derived from a fetus are found in maternal blood. The number of NRBCs derived from a fetus in maternal blood is usually smaller than the number of NRBCs of maternal origin.

[Concentration of NRBCs]

Fetal-derived cells are concentrated by a method according to this embodiment. Concentration of fetal-derived cells means acquiring a fraction in which fetal-derived cells are concentrated in a population of whole blood cells, preferably in a population of RBCs from a maternal blood sample. Further, in this embodiment, the fact that fetal-derived cells are concentrated means that the ratio of fetal-derived cells to whole blood cells in the fraction has been increased. Preferably, it means that the ratio of NRBCs to RBCs has been increased.

A fraction in which fetal-derived cells are concentrated is acquired by using a micro-channel chip. Hereinafter, the micro-channel chip is also referred to as a blood cell separation chip. Note that this name is used just for the sake of convenience. The blood cell separation chip can also separate floating cells other than the blood cells in the blood based on its three-dimensional structure. Although the material for the chip can be selected as appropriate, silicone such as PDMS is preferred.

The blood cell separation chip fractionates blood cells in a maternal sample based on the property of cells, such as the size, the plasticity, and the shape of cells. A pattern formed in a micro-channel unit of the blood cell separation chip is based on the theory of hydraulic classification described in Patent Literatures 3 and 4.

FIG. 1 shows a planer view of a blood-cell separation chip 50 as an example of the blood-cell separation chip. The blood-cell separation chip 50 includes an inlet 51, a main channel 52, a sub channel 53, and outlets 54a-54d and 55. The main channel 52 includes channels 56a to 56d successively arranged from the inlet 51 toward the outlet 55. The channels 56a to 56d are connected with one after another from the inlet 51 toward the outlet 55.

The inlet 51 shown in FIG. 1 is connected to a syringe 57 containing maternal blood. The maternal blood is sent from the syringe 57 to the inlet 51 at a predetermined volume of flow. The maternal blood enters the channel 56a through the inlet 51.

The maternal blood can be stirred. For example, a stirrer is inserted into a liquid feeding container, such as a syringe 57 shown in FIG. 1, and physically moved by an application of an external force, so that a diluted blood contained in the container can be maintained in a stirred state at all times. In this way, it is possible to prevent the distribution of blood cells from becoming uneven due to sedimentation of blood cells in the container and thereby to feed the liquid while maintaining a constant blood concentration for a long time. The stirring may be periodically performed. The stirring may be continuously performed. The stirring is performed for a part of the blood sample that is held before being injected into the chip at least when a part of the blood sample is being injected into the chip. The stirred blood sample is successively injected into the chip.

The maternal blood can to be diluted in advance. The dilution rate can be selected as appropriate. However, the dilution rate is preferably 2 to 500, preferably 4 to 50, and preferably 5 to 10. The maternal blood is diluted with phosphate buffered saline. For example, 5 to 15 ml of a diluted maternal blood can be processed in one fractionation.

The volume of flow per unit time of the diluted maternal blood can be selected as appropriate. However, the volume of flow per unit time in each micro-channel unit is preferably 0.1 to 500 μl/min, more preferably 0.5 to 50 μl/min, and particularly preferably 1 to 25 μl/min. The volume of flow may be any of 2, 3, 4, 5, 6, 7, 8, 9, 10, 11, 12, 13, 14, 15, 16, 17, 18, 19, 20, 21, 22, 23 and 24 μl/min. The volume of flow is a volume of inflow of the blood sample to the main channel.

In the case where a blood cell separation chip including a plurality of micro-channel units is used as described later, the volume of flow can be increased as appropriate according to the number of micro-channel units. However, the volume of flow is preferably one that is obtained by multiplying the aforementioned volume of flow by the number of blood cell separation chips.

The blood-cell separation chip 50 shown in FIG. 1 includes a sub channel 53. The sub channel 53 is connected to a syringe 58. The syringe 58 contains PBS (phosphate buffered saline). By applying a pressure on the syringe 58, the PBS flows through the sub channel 53 into a channel 56b. The PBS is merely an example. That is, any liquid that is unlikely to damage the cells in the blood sample due to the osmotic pressure or the pH may be used as a substitute for the PBS.

The volume of flow of the sub channel 53 is preferably 1 to 10 times the volume of flow per unit time of the blood sample to the main channel, more preferably 1 to 5 times thereof, and particularly preferably 1 to 2 times thereof. The volume of flow in the sub channel 53 is a volume of inflow of the liquid, e.g., the PBS in this example, to the sub channel 53.

Each of branch channels 59a to 59d shown in FIG. 1 is a channel branching from the main channel 52. In a channel 56c, the branch channels 59a, 59b, 59c and 59d branch from the main channel 52 one by one in this order from the upstream side. The branch channels 59a to 59d are located on the side of the main channel 52 opposite to the side thereof on which the sub channel 53 is located.

Each of the branch channels 59a to 59d shown in FIG. 1 includes a plurality of narrow channels branching from the main channel 52. These set of the narrow channels are arranged from the upstream of the main channel 52 to the downstream. The branch channels 59a to 59d extend to outlets 54a to 54d, respectively. The narrow channels of each of the branch channels 59a to 59d join together immediately before the outlets 54a to 54d, respectively. The channel 56d extends to the outlet 55.

Figure 2:
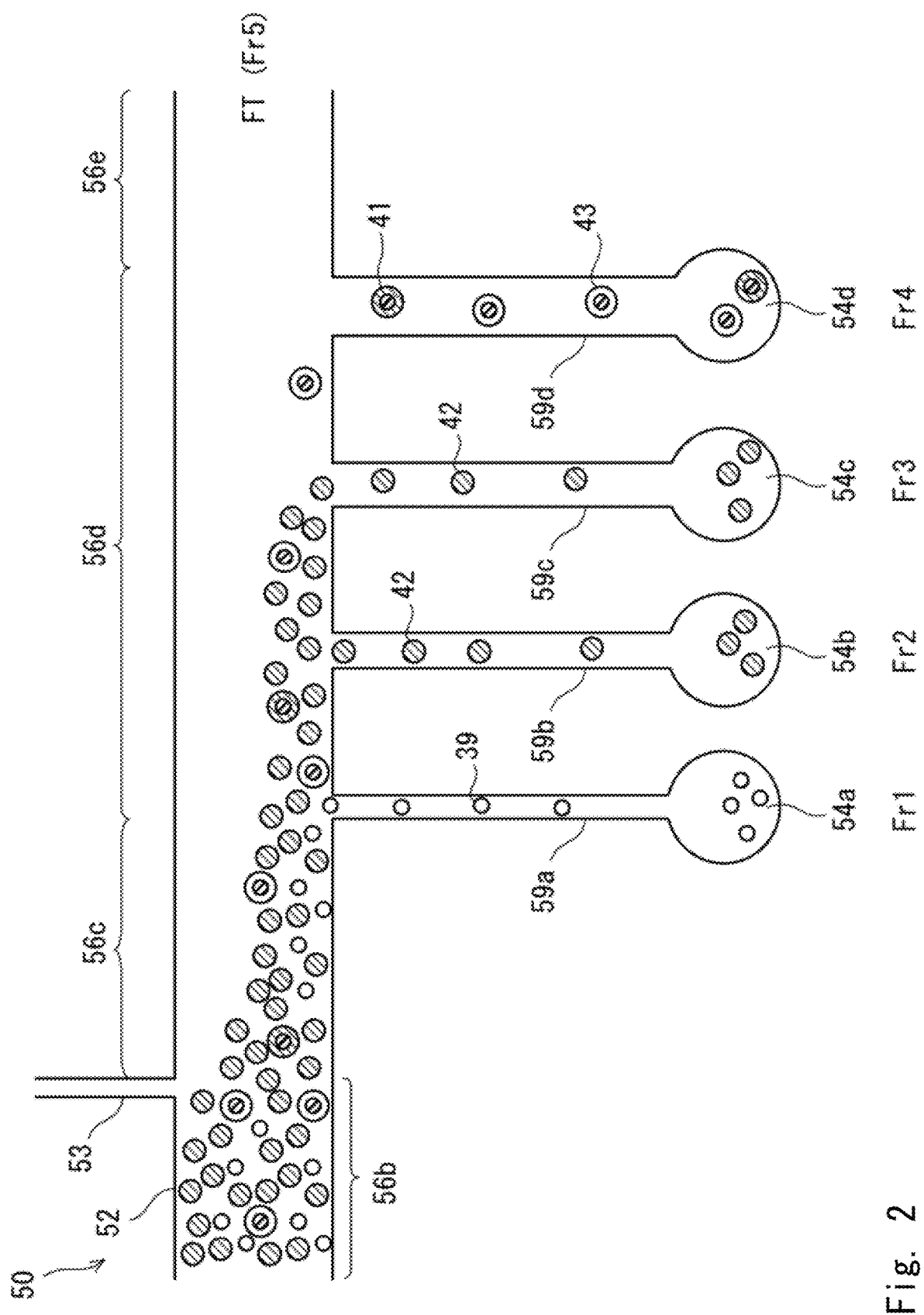
FIG. 2 is a schematic diagram of a blood-cell separation chip.

FIG. 2 schematically shows a process for fractionating blood cells by using the blood-cell separation chip 50. As shown in FIG. 1, each of the branch channels 59a to 59d includes a plurality of narrow channels. In FIG. 2, for each of the branch channels 59a to 59d, only one narrow channel is shown for simplifying the explanation.

Maternal blood flows from the upstream side of the main channel 52 shown in FIG. 2. The maternal blood contains a large number of blood cells. The blood cells reach a channel 56b. Meanwhile, PBS flowing from the sub channel 53 pushes blood cells flowing through the main channel 52 from the side of the main channel 52. In the channels 56b and 56c, blood cells are pushed toward the side of the branch channels 59a to 59d. The liquid flowing in the sub channel restrains the maternal blood by pressing.

In the channel 56a shown in FIG. 2, the branch channels 59a to 59d are arranged on the side of the main channel 52 opposite to the side thereof on which the sub channel 53 is disposed. Inscribed diameters of the narrow channels of the branch channels 59a to 59d increase according to their positions in the arrangement. Note that an inscribed diameter of a narrow channel is a diameter of an inscribed circle on an orthogonal cross section of the narrow channel. For example, the inscribed diameters of the narrow channels of the branch channels 59a to 59d may be 8, 12, 15 and 25 μm, respectively. The cross-section of a narrow channel may be a square shape, other polygonal shapes, or a circular shape. However, the cross section is preferably a square shape.

In the blood-cell separation chip 50 shown in FIGS. 1 and 2, four branch channels are provided. The branch channels 59a to 59d shown in FIG. 1 correspond to these branch channels.

Figure 11:
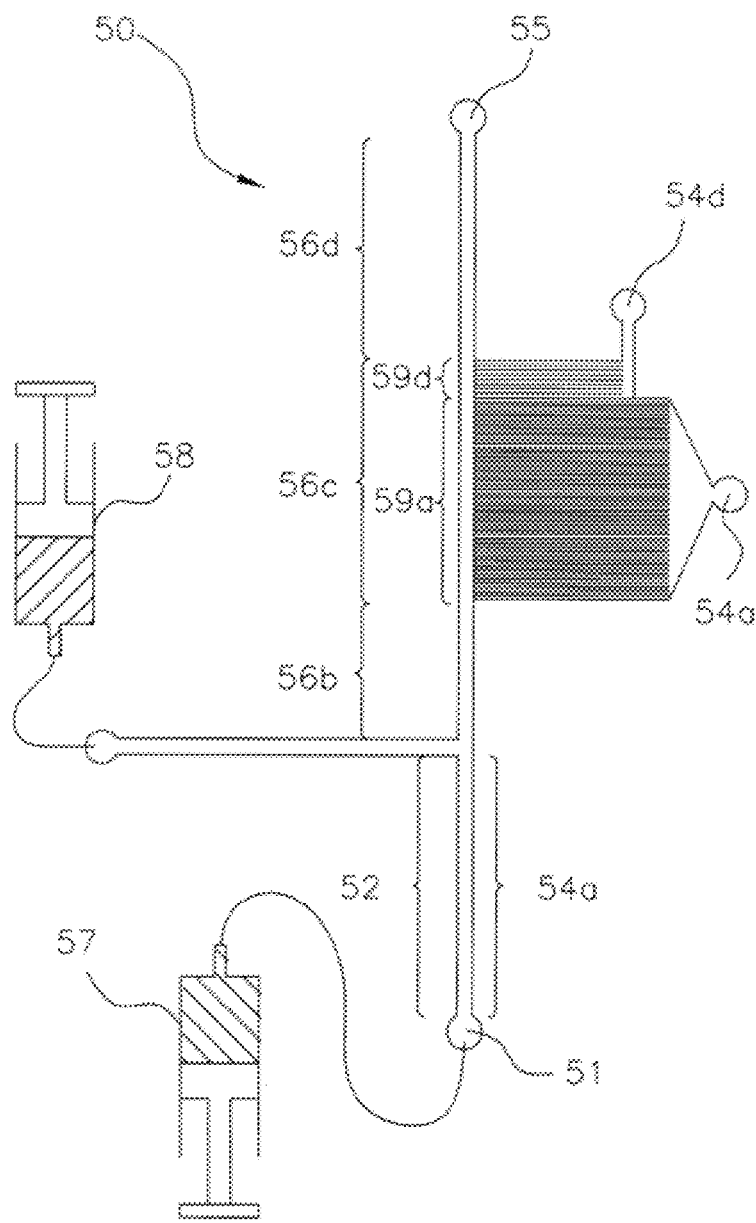
FIG. 11 is a planer view of a blood-cell separation chip.

There is no particular limitation on the number of branch channels as long as the number is not less than two. For example, at least two branch channels may be provided. These two branch channels are classified into those formed by narrow channels disposed on an upstream side and those formed by narrow channels disposed on a downstream side. The inscribed diameter of the narrow channel on the upstream side may be 4 to 19 μm and is preferably 12 to 19 μm. The inscribed diameter of the narrow channel on the upstream side may be any of 13, 14, 15, 16, 17 and 18 μm. However, the inscribed diameter is preferably any of 14, 15 and 16 μm, and more preferably 15 μm. The inscribed diameter is an inscribed diameter at the connecting part between the main channel 52 and the narrow channel. The cross-sectional area of the narrow channel may become larger toward downstream of it. Further, the downmoststream of the narrow channel may have the largest cross-sectional area. The branch channel 59a in FIG. 11 corresponds to the branch channel formed by narrow channels on the upstream side. The narrow channels on the upstream side can be regarded as a removal channel for non-nucleated RBCs. Among the blood cells pushed by the sub channel, non-nucleated RBCs enter the removal channel, so that these non-nucleated RBCs are removed from the blood sample.

Meanwhile, the inscribed diameter of the narrow channel disposed on the downstream side may be 20 to 30 μm. The inscribed diameter of the narrow channel disposed on the downstream side may be any of 21, 22, 23, 24, 25, 26, 27, 28, 29 and 29 μm. However, the inscribed diameter is preferably any of 23, 24, 25, 26 and 27 μm, more preferably any of 24, 25 and 26 μm, and particularly preferably 25 μm. The inscribed diameter is an inscribed diameter at the connecting part between the main channel 52 and the narrow channel. A cross-sectional area of the narrow channel may become larger toward downstream of it. Further, the downmost-stream of the narrow channel may have the largest cross-sectional area. The branch channel 59d in FIG. 11 corresponds to the branch channel formed by narrow channels on the downstream side. The narrow channels on the downstream side can be regarded as a collection channel for NRBCs. Among the remaining blood cells from which non-nucleated RBCs have been removed, NRBCs enter the collection channel, so that these NRBCs are acquired as a fraction from the blood sample.

The blood cells pushed by the sub channel 53 flow into the branch channels 59a to 59d shown in FIG. 2. The diameter of blood cells flowing into each branch channel is slightly smaller than the inscribed diameter of the narrow channel of that branch channel. In the figure, granules 39 are shown as blood cells slightly smaller than the inscribed diameter of the narrow channel of the branch channel 59a. The granules 39 reach the outlet 54a. In the figure, non-nucleated RBCs 42 are shown as blood cells slightly smaller than the inscribed diameters of the narrow channels of the branch channels 59b and 59c. The non-nucleated RBCs 42 reach the outlets 54b and 54c.

It is considered that the diameter of NRBCs is 11 to 13 µm. In the figure, NRBCs 41 are shown as blood cells slightly smaller than the inscribed diameter of the narrow channel of the branch channel 59d. Further, WBCs 43 are shown. The NRBCs 41 and the WBCs 43 reach the outlet 54d.

Figure 15:
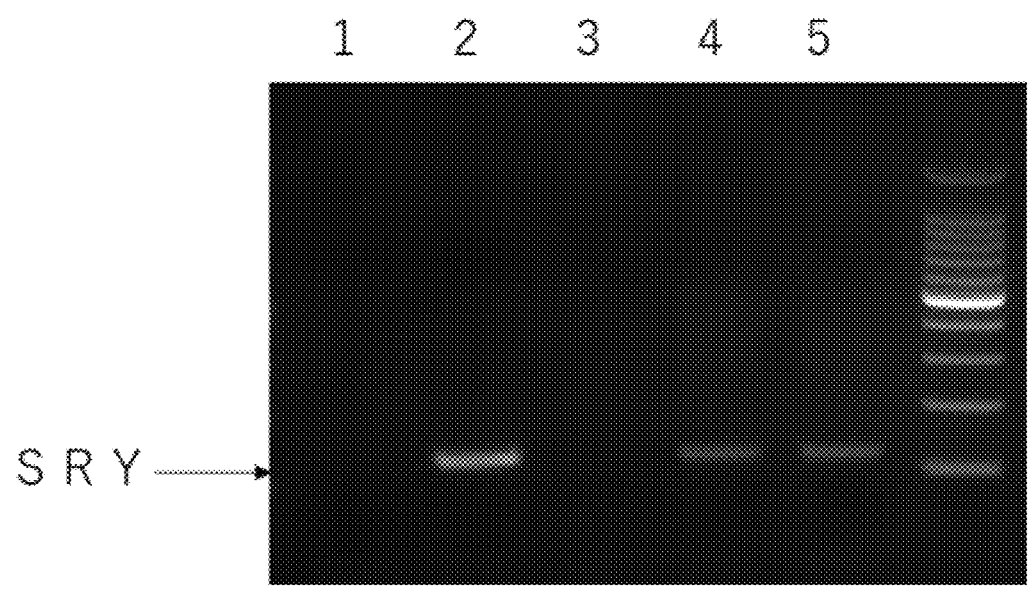
FIG. 15 is an electrophoretic image of DNA of an amplified SRY gene sequence.

The blood cells that have not taken into the branch channels 59a to 59d shown in FIG. 2 pass through the channel 56d together with plasma as flow-through (FT) and reach the outlet 55 shown in FIG. 15. For example, aggregated blood cells and the like are included in the flow-through. A reservoir for receiving fluid is provided in each of the outlets 54a to 54d and the outlet 55.

Fractions Fr1 to Fr4 are sorted out into respective reservoirs connected to the outlet 54a to 54d, respectively, shown in FIG. 2. The flow-through is sorted out as a fraction Fr5 into the reservoir connected to the outlet 55 shown in FIG. 1.

The blood cell separation chip according to this embodiment may include a plurality of micro-channel units. Each of the micro-channel units has a pattern. As shown in FIG. 2, a main channel 52, a sub channel 53, removal channels 59a to 59c, and a collection channel 59d are two-dimensionally extended in the pattern.

Figure 12:
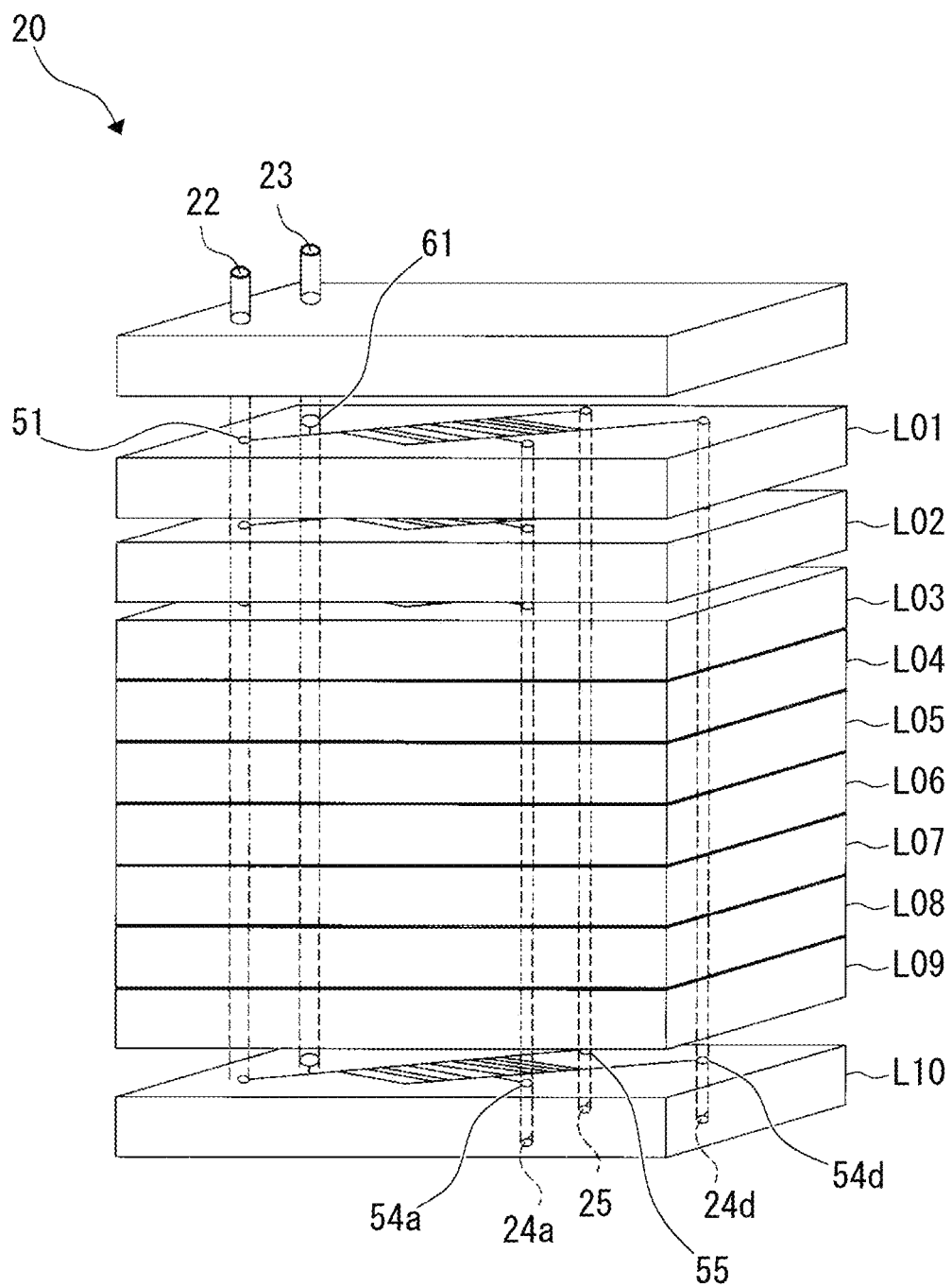
FIG. 12 is a perspective view of a multi-layered blood-cell separation chip.

A chip 20 shown in FIG. 12 is a multi-layered chip having ten layers, i.e., layers L01 to L10. Each of the layers includes a micro-channel unit. The uppermost layer of the chip 20 is a lid for the layer L01, which is the uppermost layer. The layers L01 to L10 are successively stacked at regular intervals. In the drawing, gaps between the layers L01 to L03 are large. However, this is only in the drawing and for making it easy to visually understand the shape of the pattern of the micro-channel unit. The same applies a gap between the layers L09 and L10. The number of layers of the chip 20 is merely an example. The number of layers, each of which includes the micro-channel unit, in the chip 20 is 2 to 200, preferably 5 to 50, more preferably 5 to 20, and particularly preferably 8 to 10. The number of layers may be any of 3, 4, 5, 6, 7, 8, 9, 10, 11, 12, 13, 14, 15, 16, 17, 18 and 19.

An inlet of the main channel, an inlet of the sub channel, an outlet of the removal channel, an outlet of the collection channel, and an outlet of the main channel provided in the micro-channel unit in each layer may be individually connected in that layer. As shown in FIG. 12, these inlets and outlets may be connected to respective pillar channels penetrating each layer in a traversing manner so that they are separately put together. The pillar channels may penetrate all the layers.

In FIG. 12, each of pillar channels 22 and 23 has an opening in the top surface of the chip. The pillar channel 22 is connected to inlets 51 of the main channels. The pillar channel 23 is connected to inlets 61 of the sub channels. Further, each of pillar channels 24a, 24d and 25 has an opening in the bottom surface of the chip. The pillar channel 24a is connected to outlets 54a of the removal channels. The pillar channel 24d is connected to outlets 54d of the collection channels. The pillar channel 25 is connected to outlets 55 of the collection channels. A blood sample passes through the tip 20 from the top surface of the tip 20 to the bottom surface thereof.

As shown in FIG. 12, the micro-channel units provided in the respective layers are put on top of each other in the vertical direction and thereby form a micro-channel stack. Further, when the inlets of the main channels, the inlets of the sub channels, the outlets of the removal channels, the outlets of the collection channels, and the outlets of the main channels provided in the micro-channel units in the respective layers are connected to the respective pillar channels penetrating each layer in a traversing manner so that they are separately put together, the inlet of the main channel in the bottom layer may be closed, or one of the outlets of the main channels may be closed. The outlet of the main channel in the uppermost layer or the lowermost layer may be closed.

The blood cell separation chip may include a plurality of micro-channel units in one layer. In that case, the number of micro-channel units provided in the layer may be 1 to 200, preferably 5 to 50, and more preferably 10 to 20.

The inlets of the main channels, the inlets of the sub channels, and the outlets of the main channels provided in the micro-channel units in each layer may be connected separately for each of the micro-channel units. Alternatively, the inlets and the outlets of the plurality of micro-channel units may be connected in a collective manner. The orientations and the positions of the patterns of the micro-channel units of all the layers are preferably aligned with each other in a planer view of the chip.

When the inlets of the main channels provided in all the layers are connected to one pillar channel, the volume of flow per unit time of the blood sample can be selected as appropriate. The volume of flow is preferably 0.8 to 500 µl/min, more preferably 4 to 200 µl/min, and particularly preferably 8 to 25 µl/min. The volume of flow may be any of 1, 2, 3, 4, 5, 6, 7, 8, 9, 10, 11, 12, 13, 14, 15, 16, 17, 18, 19, 20, 21, 22, 23 and 24 µl/min. The volume of flow is a volume of inflow of the blood sample to the pillar channel.

Further, when the inlets of the sub channels provided in all the layers are connected to one pillar channel, the volume of flow per unit time of the liquid fed to the pillar channel of the sub channels may be adjusted as follows. The volume of flow is preferably 1 to 10 times the volume of flow per unit time of the blood sample fed to the main channel, more preferably 1 to 5 times thereof, and particularly preferably 1 to 2 times thereof. The volume of flow may be any of 1.1, 1.2, 1.3, 1.4, 1.5, 1.6, 1.7, 1.8 and 1.9 times. The liquid may be PBS.

The concentration method according to this embodiment has advantages as compared to the method using the density. One of the advantages is that while the influence of the elapsed time after the blood collection on the density of blood cells is large, the influence thereof on the size of blood cells is small. This means that even when the place where blood is collected is distant from the place where blood cells are fractionated, the method according to this embodiment can be easily carried out. Another advantage is that the fractionation based on the size can be performed though easy operations, such as through operations of the above-described blood cell separation chip.

[Fluorescence Labeling of Fractions A]

NRBCs in a fraction in which the NRBCs have been concentrated by using the blood cell separation chip according to this embodiment (hereinafter also referred to as a fraction A) may be further concentrated by cell sorting.

At least WBCs and nucleic acids in the fraction A are specifically labeled. RBCs may be specifically labeled. The labeling (label or labeling) may be magnetic labeling or fluorescent labeling, though the fluorescent labeling is preferred. The labeling may be direct labeling or indirect labeling. The indirect labeling may be labeling made by a tag and a secondary antibody, or may be labeling made by a biotin-avidin bonding.

The labeling specific to WBCs may be immunolabeling. This labeling may be labeling for an antigen specific to WBCs such as CD45. The antigen may be a sugar chain antigen.

The labeling specific to RBCs may be labeling specific to surfaces of RBCs. The labeling specific to RBCs may be immunolabeling. The immunolabeling may be labeling made by an antibody. A target antigen of the immunolabeling may be a sugar chain antigen. The labeling may be labeling made by an antibody for an antigen specific to RBCs such as CD71 and CD235a (GPA, Glycophorin A).

The immunolabeling specific to RBCs may be labeling specific to premature RBCs. It may be immunolabeling whose target antigen is a peptide chain specific to premature RBCs, such as an embryonic epsilon globin chain of hemoglobin. Such antibodies for immunolabeling are mentioned in Patent Literature 5.

Nuclei contained in NRBCs are specifically labeled by labeling specific to nucleic acids. The labeling specific to nucleic acids may be dye labeling. The nucleic acids to be labeled are preferably DNA. The dye may be a fluorescent dye. Nuclei may be fluorescent-labeled by a fluorescent dye. The fluorescent dye may be Hoechst33342.

Further, an antibody that reacts with a surface antigen present on fetal NRBCs but does not react with a surface antigen present on maternal RBCs may be used. The antibody may be a monoclonal antibody. For example, it may be an antibody 4B9 mentioned in Patent Literature 6. The aforementioned antibodies may be used together with the aforementioned immunolabeling specific to RBCs or the labeling specific to nucleic acids. By using such an antibody, it is possible to perform labeling specific to NRBCs without relying on the labeling specific to nucleic acids.

Note that histological crosslinking-fixing may be performed for blood cells in the fractions A before one of the above-described labeling processes is performed. Alternatively, the crosslinking-fixing may be performed for blood cells in the fractions A before any of the above-described labeling processes is performed. Further, the below-described fractionation by cell sorting may be performed in this state. It is possible to prevent blood cells from aggregating by crosslinking/fixing blood cells. Therefore, the sorting by cell sorting can be accurately performed.

The below-described fractionation, i.e., fractionation by cell sorting may be performed without performing histological crosslinking/fixing for blood cells in the fraction A.

For example, labeling specific to nucleic acids and labeling specific to RBCs may be performed at the same time without performing crosslinking/fixing of blood cells. Further, blood cells may be crosslinked/fixed after these labeling processes are performed. Further, immunolabeling specific to WBCs may be performed for crosslinked/fixed blood cells.

[Further Concentration of NRBCs by Cell Sorting]

NRBCs can be further concentrated by sorting out labeled blood cells in the fraction A by cell sorting. In the cell sorting, for example, an apparatus used for sorting out cells (e.g., a cell sorter) is used. In the case where the labeling is fluorescent labeling, the sorting method by cell sorting may be a fluorescence activated cell sorting (FCM) method. The sorting method by cell sorting may be a cell sorting method by using magnetic labeling. In this embodiment, there are no particular limitations on the principle of the cell sorting and the type of the cell sorter.

In an aspect, the FCM is performed by a cell analyzer equipped with a sorting apparatus, for example, by a cell sorter. In an aspect, the cell sorter makes cells carried by a continuously-flowing fluid and identifies features of individual cells based on fluorescence of the cells that is generated by irradiating the cells with excitation light. This identification is also a function of the cell analyzer. Based on information obtained by the identification, the cell sorter further confines cells in droplets and collects droplets containing specific cells. By doing so, the cell sorter sorts out the specific cells In an aspect, the cell sorter makes cells carried by a continuously-flowing fluid and identifies features of individual cells based on fluorescence of the cells that is generated by irradiating the cells with excitation light. Based on information obtained by the identification, the cell sorter sorts out fractions containing specific cells in a state in which cells are continuously carried by the continuously-flowing fluid.

Figure 3:
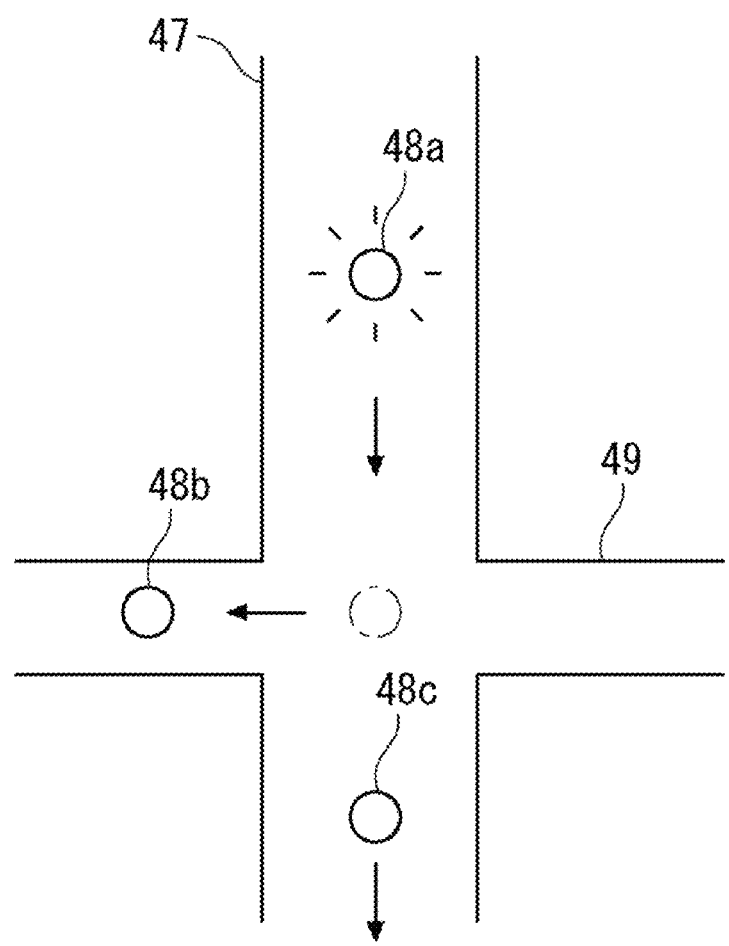
FIG. 3 is a schematic diagram of a cell sorter.

As the above-described cell sorter that does not use droplets, a cell sorter that use pulsed flows for the sorting has been known as shown in the later-described FIG. 3 and as disclosed in Patent Literature 7. Further, a cell sorter that uses a sol-gel transition of a fluid for the sorting has been known as disclosed in Patent Literature 8.

In the case of the above-described cell sorter that does not use droplets, since cells can be guided into sorting containers while keeping the cells carried by the fluid, the cells are less likely to be damaged. Further, it is easy to prevent the apparatus and the environment from being contaminated due to splashing of the fluid by confining the fluid in a channel chip during the process for guiding cells to containers.

In the cell sorting, blood cells are preferably sorted out so that blood cells that have been labeled with the label specific to RBCs are obtained. Since NRBCs are RBCs, the NRBCs can be distinguished from other blood cells including WBCs by labeling specific to RBCs. WBCs labeled by labeling specific to WBCs may be removed from the fraction A.

In the cell sorting, the blood cells are preferably sorted out so that blood cells that have been labeled with the label specific to nucleated blood cells are obtained. Since NRBCs have nuclei, the NRBCs can be distinguished from other blood cells including non-nucleated RBCs by the labeling specific to nucleic acids.

In the cell sorting, a fraction having increased purity of NRBCs is obtained by combining the above-described labeling processes. The sorting by the labeling specific to RBCs and the sorting by the labeling specific to nucleic acids may be performed at the same time. Alternatively, one of the sorting processes may be performed before the other sorting. For example, a fraction B may be obtained by first performing sorting by magnetic labeling specific to RBCs and then performing sorting by using fluorescent labeling specific to nucleic acids.

[Additional Cell Selection]

When blood cells in the fraction A are fluorescent-labeled, the FACS (Trademark) is preferably used as the cell sorting. Further, since the fluorescent label remains even after the cell-sorting process, this fluorescent label may be effectively used.

For example, cells may be further sorted out by additionally using fluorescence for the first fraction obtained by the cell sorting. For example, the second and subsequent fractions may be obtained by further repeating the sorting by the cell sorting for the obtained first fraction. In this way, the aforementioned fraction B may be eventually obtained.

[Provision of Data for Diagnosis]

It is possible to efficiently concentrate NRBCs from a blood sample in a short time by the method according to this embodiment. In particular, when maternal blood is used as the blood sample, it is possible to concentrate fetal-derived NRBCs in a short time. A nuclear genome of fetal-derived NRBCs may be analyzed by one of a fluorescence in situ hybridization (FISH) method, a next generation sequencing (NGS) method, and a micro array method. By the analysis, data about the number of chromosomes, the structure of chromosomes, and the base sequence of nuclear genomic DNA can be acquired. Such data can be used for testing or a diagnosis for a chromosomal disease of a fetus. This testing is noninvasive prenatal genetic testing.

In the in-situ hybridization method, an oligonucleotide probe labeled with a fluorescent substance or an enzyme is used. Expression of a gene of interest is analyzed by hybridizing the oligonucleotide probe with the gene of interest and then detecting this probe. Among such methods, those in which the probe is labeled with a fluorescent substance are called fluorescence in situ hybridization methods. Data for diagnosis can be acquired by the fluorescence in situ hybridization method. The data for diagnosis is useful for determining the presence/absence of an abnormality in the chromosomal number or disorders caused by the deletion of a small piece of chromosome, such as Down's syndrome, Edwards' syndrome, and 22q11.2 deletion syndrome.

The data for diagnosis may be obtained by analyzing concentrated NRBCs by the in-situ hybridization method. For example, data to be used for a diagnosis of Down's syndrome can be acquired by performing the FISH using a fluorescent probe based on a DNA sequence specific to Chromosome 21.

The next generation sequencing method is a method in which a base sequence of DNA is read at a high speed. Data for diagnosis can be obtained by reading a base sequence of nuclear genomic DNA contained in concentrated fetal-derived NRBCs by the NGS. The data for diagnosis is useful for determining the presence/absence of an abnormality in the chromosomal number or disorders caused by the deletion of a small piece of chromosome, such as Down's syndrome, Edwards' syndrome, and 22q11.2 deletion syndrome.

The data for diagnosis may be obtained by analyzing nuclear genome DNA of fetal-derived NRBCs by the microarray method. The microarray method is performed for a minute spot on a substrate by hybridizing each genomic DNA or its amplified DNA that has been, for example, fluorescent-labeled in advance. Synthetic DNA having a gene sequence has been adsorbed in advance in the spot. The data for diagnosis is useful for determining the presence/absence of an abnormality in the chromosomal number or disorders caused by the deletion of a small piece of chromosome, such as Down's syndrome, Edwards' syndrome, and 22q11.2 deletion syndrome.

A half of the chromosomes of fetal-derived NRBCs are the same as those of mother's body. Therefore, the background signal of the maternal chromosome sequence has a large influence on the analyses by the FISH, the NGS, and the microarray method. Meanwhile, the number of NRBCs contained in the maternal blood is very small. Meanwhile, the method according to this embodiment can efficiently concentrate NRBCs. Therefore, the method according to this embodiment is suitable for preparing fetal-derived NRBCs used for these analysis means.

EXAMPLES

This embodiment will be described hereinafter in a more detailed manner by showing examples. These examples are not intended to limit the present invention.

Reference Example 1

<Blood Collection>

In this reference example and later-described examples, maternal blood and ordinary blood are obtained under legitimate procedures. The maternal blood was provided by a pregnant woman in 33th week of pregnancy for testing and research. The sex of the fetus was male. The ordinary blood used in this example was provided by a person who was not pregnant for testing and research. The maternal blood and the ordinary blood were collected in medical institutions (facilities). These blood samples were transported to a laboratory of the inventor et al. under appropriate management.

In this example, 20 ml of maternal blood was used as a starting material and its process was started two hours after the collection of the blood.

According to measurement by a fully-automatic cell counter TC20 (BIORAD), $3.16 \times 10^{10}$ blood cells were contained in every 10 ml of maternal blood. The maternal blood was diluted with the same volume of PBS (phosphate buffered saline).

<Concentration of NRBCs>

NRBCs in the maternal blood were concentrated by a density gradient centrifugation method. Note that the concentration means removing blood cells other than NRBCs. The blood cells that are removed from the maternal blood during the concentration are preferably non-nucleated RBCs. More preferably, platelets are also removed from the maternal blood during the concentration.

A fraction A in which NRBCs were concentrated was obtained by a density gradient layered centrifugation method. After the concentration, a ratio of NRBCs to all the blood cells in the fraction A is higher than a ratio of NRBCs to all the blood cells in the maternal blood sample.

The fractionation by the density gradient layered centrifugation method was performed as follows. Isotonic solutions having densities of 1.085 g/ml and 1.075 g/ml were prepared by using percoll and saline. After stacking them one by one in a centrifuge tube, 10 ml of maternal blood was further layered. The centrifuge tube was centrifuged with 1,750 G at 20° C. for 30 minutes.

Figure 4:
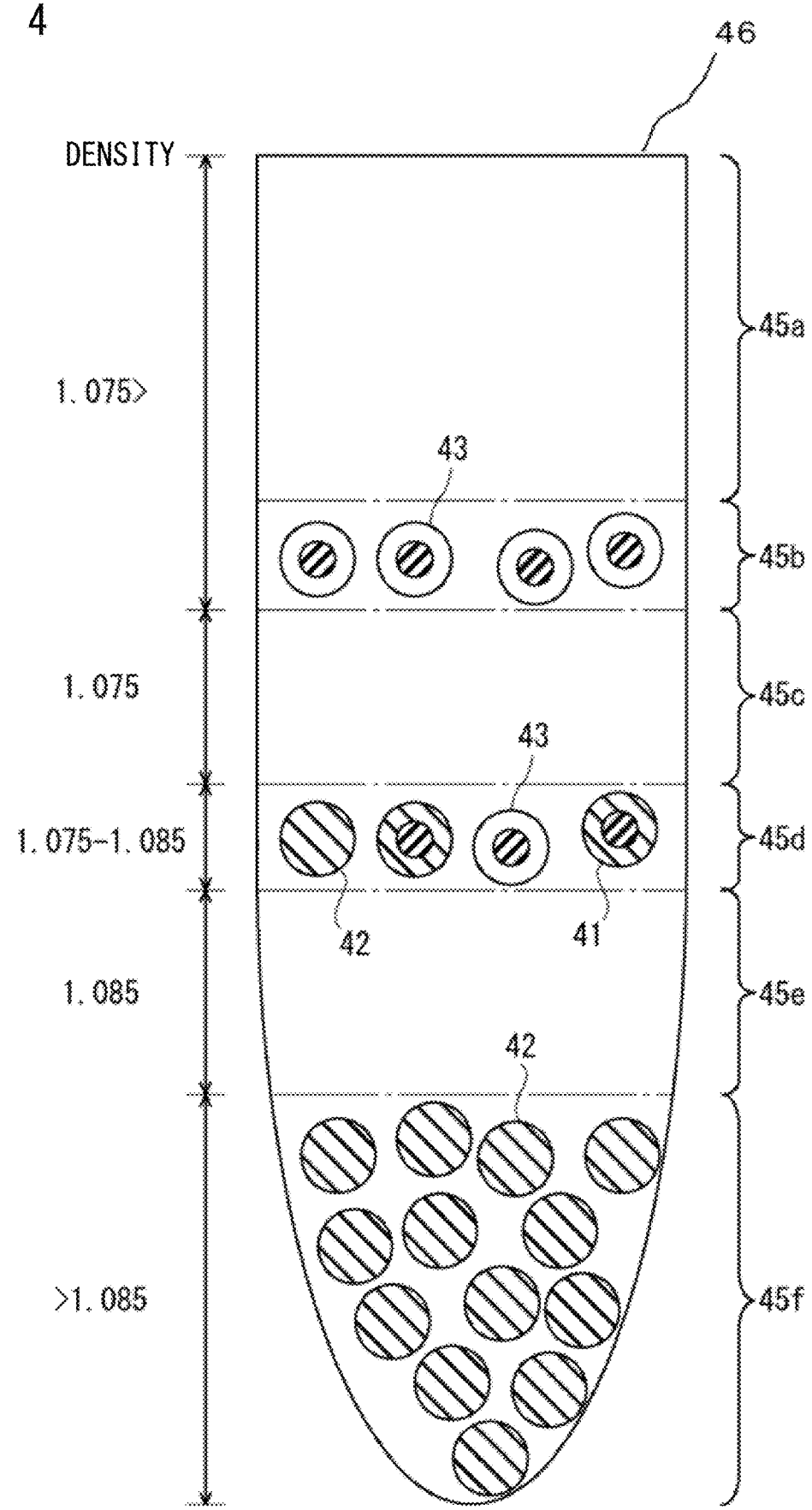
FIG. 4 is a schematic view showing a result of a density gradient centrifugation.

FIG. 4 shows a schematic diagram showing a result of the density gradient layered centrifugation. From the top of the centrifugal tube 46, layers 45a to 45f are formed one after another. Plasma is concentrated in the layer 45a. WBCs 43 are concentrated in the layer 45b. It is presumed that the densities of the layers 45a and 45b are smaller than 1.075 g/ml. The layer 45c is a layer of an isotonic solution having a density of 1.075 g/ml.

NRBCs 41 are concentrated in the layer 45d shown in FIG. 4. It is presumed that the density of the layer 45d is larger than 1.075 g/ml and smaller than 1.085 g/ml. A fraction containing NRBCs was obtained by sorting out blood cells from the layer 45d and washing the blood cells. This fraction was referred to as a sample 1. The number of blood cells in the sample 1 was measured by using a fully-automatic cell counter TC20. The number of blood cells was about $9.95 \times 10^6$.

The layer 45e shown in FIG. 4 is a layer of an isotonic solution having a density of 1.085 g/ml. Non-nucleated RBCs 42 are concentrated in the layer 45f. It is presumed that the density of layer 45f is larger than 1.085 g/ml.

A half of the sample 1 was used as a fraction A and the following steps for fluorescent labeling were performed.
<Fluorescent Labeling>

Blood cells in the fraction A were simultaneously stained with Hoechst33342 (manufactured by Sigma-Aldrich), an anti-CD45-PE labeled antibody (manufactured by Miltenyi-Biotec, clone name: 5B1), and an anti-CD235a-FITC labeled antibody (Miltenyi-Biotec, clone Name: REA175). Crosslinking/fixing of blood cells was not performed in the staining process. The staining was performed at 4° C. for 10 minutes. After the staining, labeled blood cells were collected by centrifuging a suspension of blood cells with 300 G at 4° C. for 10 minutes.

Regarding the dilution of the antibody, a volume ratio (i.e., a dilution ratio) between the anti-CD45-PE labeled antibody and the buffer solution was 1:10. Further, a volume ratio (i.e., a dilution ratio) between the anti-CD235a-FITC labeled antibody and the buffer solution was 1:1099.

The fraction A was further fractionated by cell sorting. As a cell sorter, a cell sorter shown in a schematic diagram of FIG. 4 was used. This cell sorter is used to detect fluorescence of blood cells.

Firstly, a steady liquid flow containing the fluorescent-labeled fraction A is generated in a main channel 47 shown in FIG. 4. Excitation light is applied to a blood cell 48a in the liquid flow and the presence or absence of a signal of the label is detected based on fluorescence. A sub channel 49 intersects the main channel 47. The blood cell 48a flows toward the intersection between the main channel 47 and the sub channel 49.

A blood cell 48b shown in FIG. 4 is a blood cell for which the signal is detected. This blood cell flows through the main channel 47 and enters the intersection. In the sub channel 49, a pulsed flow can be generated in a direction intersecting the liquid flow. Based on the aforementioned signal, a pulsed flow is generated with the blood cell 48b being its target.

By making the blood cell 48b shown in FIG. 4 carried by the pulsed flow through the sub channel 49, the blood cell 48b is separated from the liquid flow through the main channel 47. Separated blood cells 48b are successively collected. In this way, a fraction B composed of collected blood cells 48b is generated.

In FIG. 4, no pulsed flow is generated for a blood cell 48c for which no signal is detected or the signal is weak. The blood cell 48c is continuously carried by the liquid flow and flows through the main channel 47.

Details of the above-described cell sorter are described in Patent Literature 7. Further, in this example, a cell sorter available from On-chip Biotechnologies Co., Ltd. was used (Cell sorter model: On-chip-Sort MS6). In this reference example, the operating conditions of the cell sorter for cell sorting were as follows.
<Analysis by Cell Sorting>

Figure 5:
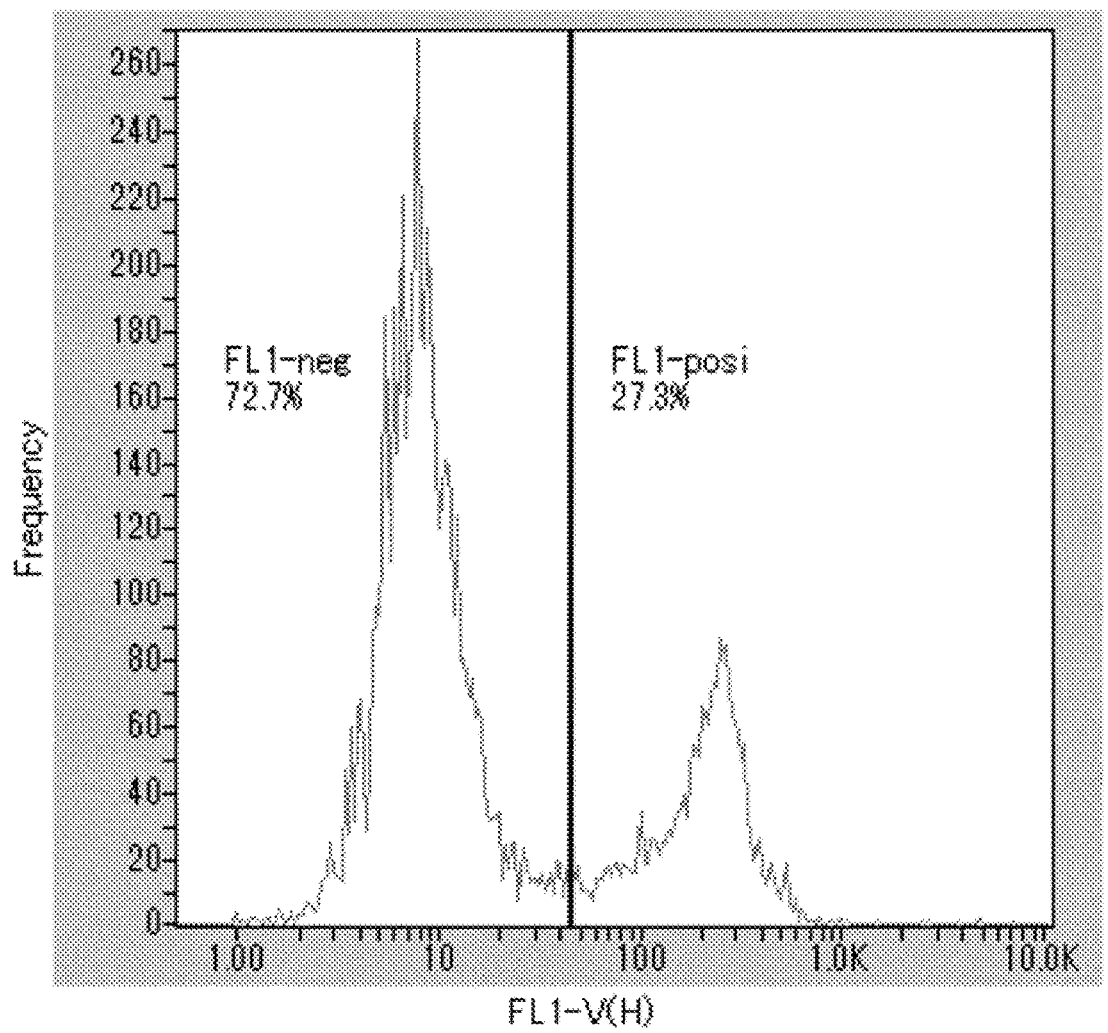
FIG. 5 shows a fluorescence intensity distribution of Hoechst33342.

FIG. 5 shows a fluorescence intensity distribution of Hoechst33342. A vertical axis represents frequencies of appearances of blood cells. A horizontal axis represents intensities of fluorescence signals of Hoechst. There are two peaks. The lowest frequency of appearances was observed between intensities 40 and 50. A border value was defined based on this range, and it was presumed that blood cells for which signal intensities are higher than this border value were nucleated blood cells. Further, it was presumed that blood cells for which signal intensities are lower than this border value were non-nucleated blood cells.

Figure 6:
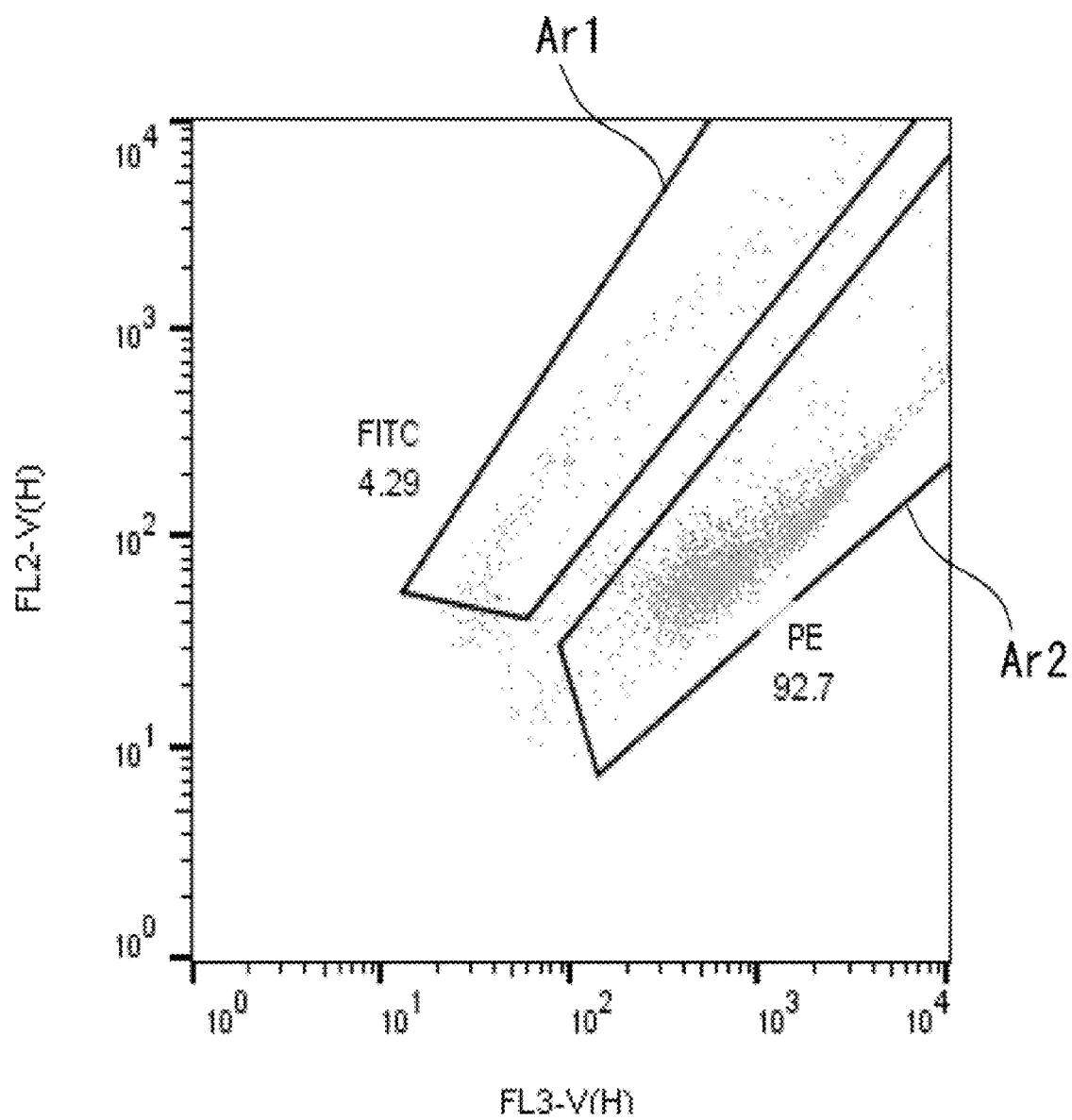
FIG. 6 shows a fluorescence intensity distribution of immunolabeling in maternal blood.
Figure 7:
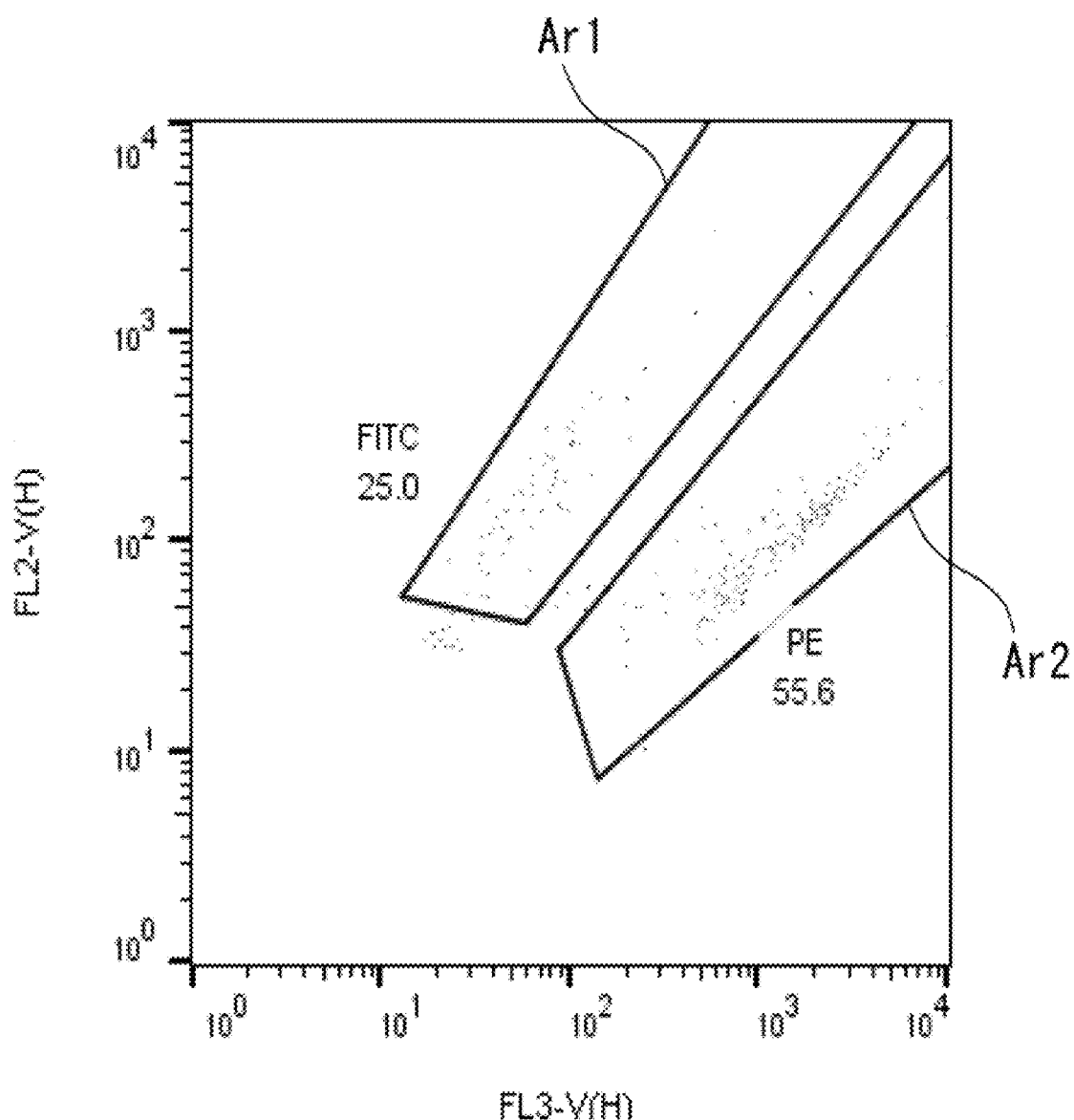
FIG. 7 shows a fluorescence intensity distribution of immunolabeling in ordinary blood.

FIG. 6 shows a fluorescence intensity distribution of immunolabeling in maternal blood. FIG. 7 shows a fluorescence intensity distribution of immunolabeling in ordinary blood. A vertical axis represents intensities of luminescence signals of FITC (fluorescein isothiocyanate) bonded with an anti-CD235a antibody. A horizontal axis represents intensities of luminescence signals of PE (phycoerythrin) bonded with an anti-CD45 antibody.

Ar1 in FIGS. 6 and 7 represents a group of cells in which signals of CD235a-FITC were strong. Ar2 represents a group of WBCs labeled with CD45.

Based on a comparison between the result of the maternal blood and the result of the ordinary blood, it was found that the number of blood cells belonging to the group Ar1 in the maternal blood is larger than that in the ordinary blood.

In FIG. 6, cells in the group Ar1 for which luminescence signal intensities of FITC (fluorescein isothiocyanate) were higher than $1 \times 10^3$ were selected as candidates for NRBCs. This threshold was determined based on the fact that background noises, i.e., luminescence signal intensities of FITC of WBCs in a preliminary experiment were $1 \times 10^3$ or lower.
<Molecular Biological Analysis>

DNA was extracted from the whole fraction B by using Nucleospin Tissue XS (purchased from Takara Bio Inc.).

Figure 14:
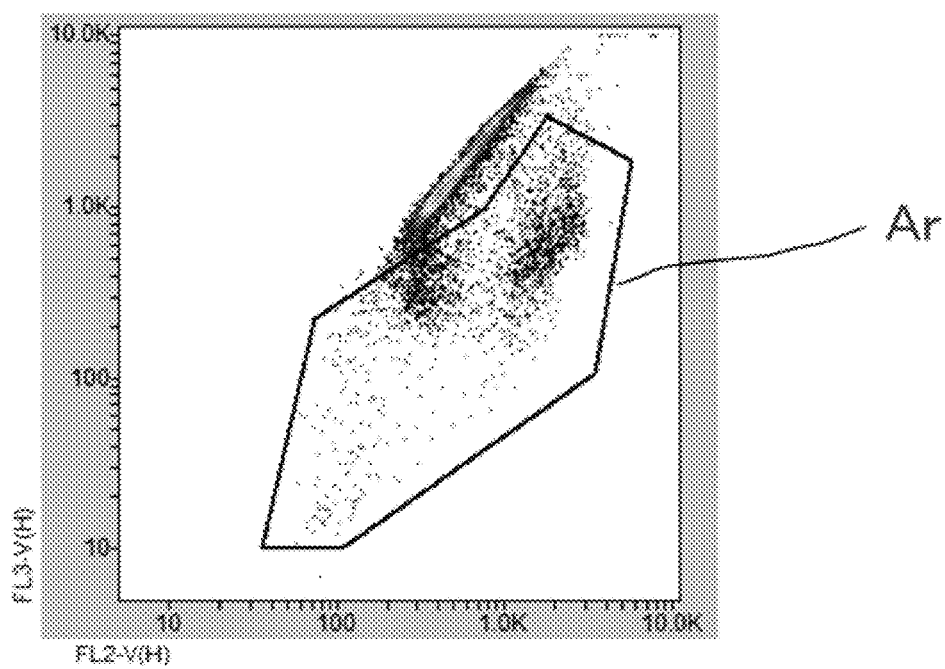
FIG. 14 shows a fluorescence intensity distribution of immunolabeling of Fr2.

In this example, a PCR reaction was performed by using the DNA obtained by the DNA extraction as a template. In the PCR reaction, Ex-Taq polymerase was used. FIG. 14 shows a result of the molecular biological analysis. Lanes 1 to 11 in an electrophoretic image shown in FIG. 8 indicate amplification products having a length of 270 bp obtained by the PCR for an SRY gene sequence. The templates are as follows.

200 bp DNA ladder is shown on the left side of the lane 1.

Lane 1: Standard DNA of Human male, 200 copies.
Lane 2: Standard DNA of Human female, 200 copies.
Lane 3: Standard DNA of Human male, 0 copies.
Lane 4: Standard DNA of Human male, 1 copy.
Lane 5: Standard DNA of Human male, 4 copies.
Lane 6: Standard DNA of Human male, 8 copies.
Lane 7: Standard DNA of Human male, 16 copies.
Lane 8: Standard DNA of Human male, 64 copies.
Lane 9: Standard DNA of Human male, 100 copies.
Lane 10: Sample 1

Figure 8:
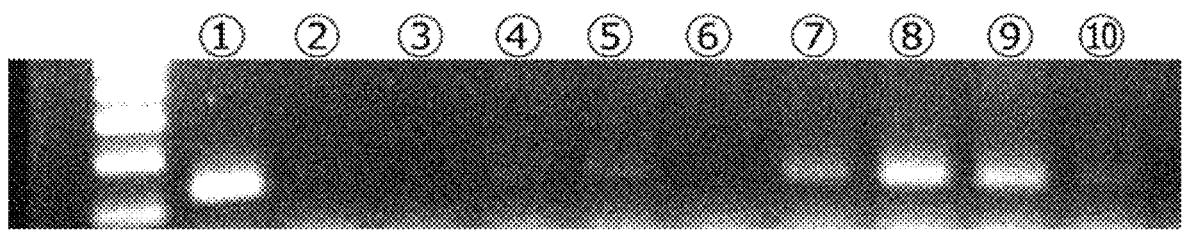
FIG. 8 is an electrophoretic image of DNA of an amplified SRY gene sequence.

From the electrophoretic image shown in FIG. 8, it was found that the sample 1 contained DNA having 4 to 16 copies of the SRY gene sequence. Therefore, it was found that the sample 1 contained chromosomal DNA derived from the fetus.

Example 1

<Concentration of NRBCs by Blood Cell Separation Chip>

In an Example 1, by using 0.3 ml of maternal blood two to three hours after the blood was collected, NRBCs were concentrated by using the blood cell separation chip shown in FIGS. 1 and 2.

The maternal blood was diluted to 50 times in advance. The maternal blood was diluted with phosphate buffered saline (PBS). Both of the volume of flow per unit time of the diluted maternal blood to the main channel and that of the PBS to the side channel in each blood cell separation chip were adjusted to 25 µl/min. Fractionation using the blood-cell separation chip was performed for ten hours.

In this embodiment, four branch channels (59a to 59d) are provided as shown in FIG. 2. Further, the inscribed diameters of narrow channels of these branch channels were 8, 12, 15 and 25 µm, respectively. In this example, the cross section of the narrow channel was square.

<Fractionation>

A Table 1 shows a result of fractionation of 15 ml of diluted maternal blood using the above-described blood-cell separation chip. The maternal blood contained 300 µl of maternal whole blood. It is presumed that $1.43 \times 10^9$ blood cells are contained in the maternal whole blood. Measurement was carried out by using a fully-automatic cell counter TC20. The Table 1 shows the numbers of blood cells of fractions that passed through branch channels 1 to 4, and a flow-through 5.

TABLE 1

| | Diameter of Channel (µm) | Number of Blood Cells | Ratio (%) |
|---|---|---|---|
| Fr1 | 8 | $8.46 \times 10^7$ | 18 |
| Fr2 | 12 | $1.48 \times 10^8$ | 32 |
| Fr3 | 15 | $1.97 \times 10^8$ | 45 |
| Fr4 | 25 | $3.29 \times 10^7$ | 7 |
| Fr5 | FT | $7.93 \times 10^5$ | 0 |

The number of blood cells in a fraction Fr4 shown in the Table 1 was $3.29 \times 10^7$. In consideration of the result of the density gradient layered centrifugation, it is considered that this fraction contains blood cells corresponding to NRBCs and WBCs. The fraction Fr4 was used as the above-described fraction A and analyzed by cell sorting.

A fraction B was sorted out in a manner similar to the Reference Example 1. Firstly, the fraction A was stained with Hoechst33342 and a PE-labeled anti-CD45 antibody. The staining was carried out without performing a fixing process including crosslinking/fixing for cells. Next, staining with an FITC-labeled anti-CD235a antibody was performed. The concentration of the antibody was optimized in a manner similar to the Reference Example 1.

Then, $3.29 \times 10^7$ blood cells of the fraction Fr4 were sorted out by a cell sorter available from On-chip Biotechnologies Co., Ltd. Blood cells that were positive for Hoechst33342 and CD235a and negative for CD45 were sorted out. Through the above-described processes, a fraction containing 661 blood cells was obtained.

<Separation at Single-Cell Level>

Figure 9:
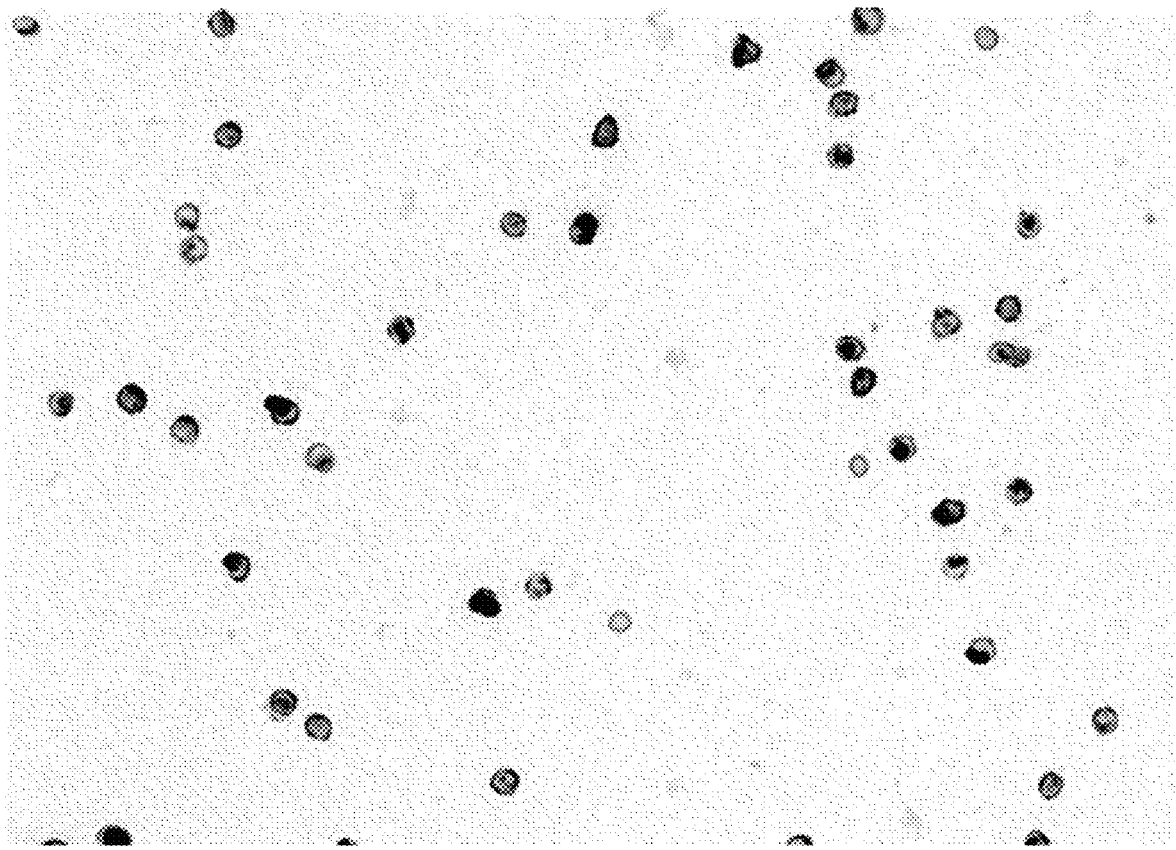
FIG. 9 is a stained image of blood cells.

FIG. 9 shows blood cells that were stained as described above. As shown in the figure, formation of aggregations was prevented. Therefore, it has been shown that blood cells can be separated from each other at a single-cell level. It is considered that aggregations were prevented in this example because the concentration of the antibody with which blood cells were stained was optimized.

<Extraction of Chromosomal DNA>

The above-described fraction B was divided into three fractions each of which contained 200 blood cells. Each of these fractions was expected to contain one or two NRBCs derived from a fetus.

Figure 10:
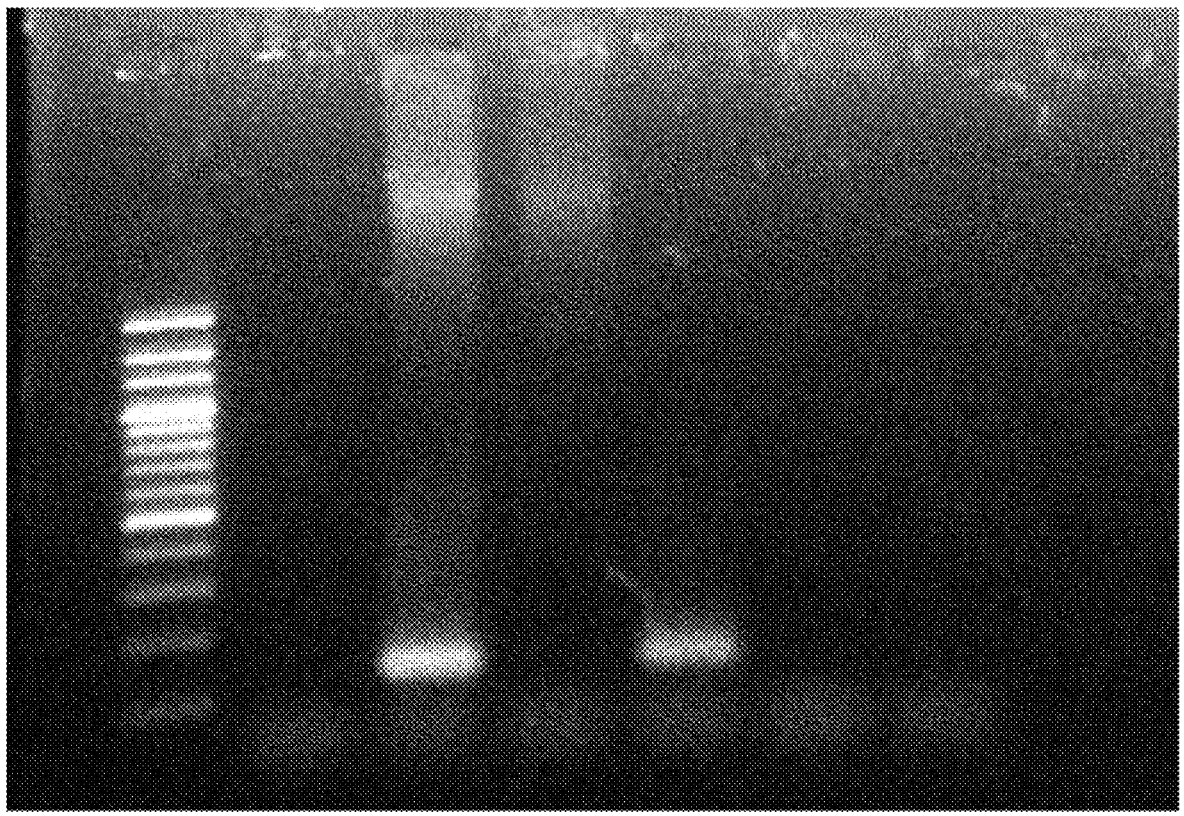
FIG. 10 is an electrophoretic image of DNA of an amplified SRY gene sequence.

Chromosomal DNA was extracted from each fraction. Whole genome amplification was performed for the chromosomal DNA by an MALBAC (Multiple Annealing and Looping Based Amplification Cycles) method. By doing so, a Y-chromosome derived from a fetus was amplified, thus making it possible to easily detect an SRY gene in a later process. Using the amplified chromosomal DNA as a template, PCR amplification specific to an SRY gene sequence was performed. FIG. 10 shows an electrophoretic image of a PCR product of the SRY gene. Templates are as follows.

200 bp DNA ladder is shown on the left side of a lane 1.
Lane 1: distilled water.
Lane 2: Standard DNA of Human male, 20 ng.
Lane 3: Standard DNA of Human female, 20 ng.
Lane 4: Amplification product 1 by MALBAC method, 450 ng.
Lane 5: Amplification product 2 by MALBAC method, 610 ng.
Lane 6: Amplification product 3 by MALBAC method, 700 ng.

An SRY band was observed in lane 4, in which PCR was performed with the amplification product 1 as a template. No SRY band was observed in the PCR in which the other amplification products were used as the template. From the above-described matters, it has been found that it is possible to fractionize and thereby divide the fraction B into a fraction containing blood cells derived from a fetus and a fraction containing no blood cell derived from a fetus.

From the above-described facts, it was confirmed that NRBCs can be concentrated by the blood cell separation chip according to this embodiment.

Example 2

<Concentration of NRBCs by Blood Cell Separation Chip>

Maternal blood provided from a 43-year-old woman in 26th week of pregnancy (the fetus was male) was diluted to five times with PBS and NRBCs were concentrated by using a blood cell separation chip. The maternal blood that was diluted about 69 hours after the collection of blood was used.

The used blood cell separation chip was one that was obtained by modifying the blood cell separation chip used in the Example 1. While the chip used in the Example 1 had four branch channels and a flow-through, a chip in which ten layers each of which has two branch channels having inscribed diameters of 15 µm and 25 µm, respectively, and a flow-through (59a and 59d in FIG. 11) are stacked on top of each other was used in this example. That is, the following chip was used, i.e., a chip in which: all channels are two-dimensionally arranged in a micro-channel unit; the separation chip includes ten layers each of which includes a micro-channel unit; the micro-channel units provided in the respective layers are put on top of each other in a vertical direction and thereby form a micro-channel stack; in layered channels, inlets of main channels, inlets of sub channels, outlets of removal channels, outlets of collection channels, and outlets of the main channels provided in the micro-channel units in the respective layers are connected to respective pillar channels penetrating all the layers so that they are separately put together: and the inlet of the main channel in the bottom layer is closed and one of the outlets of the main channels is closed (FIG. 12).

Both of the volume of flow per unit time of the diluted maternal blood and that of the PBS to the sub channel in each blood cell separation chip were adjusted to 50 µl per minute, and fractionation was performed for 60 minutes by using the blood cell separation chip. Table 2 shows the numbers of blood cells of fractions that passed through a branch channel 1 (Fr1), a branch channel 2 (Fr2), and a flow-through 3 (Fr3), respectively.

TABLE 2

| Fraction | Number of Cells (cells) | Ratio (%) |
|---|---|---|
| Fr1 | $1.19 \times 10^9$ | 96.00% |
| Fr2 | $3.11 \times 10^7$ | 2.52% |
| Fr3 | $1.83 \times 10^7$ | 1.48% |
| Total | $1.24 \times 10^9$ | 100.00% |

It was considered that the obtained fraction 2 contained $3.11 \times 10^7$ blood cells. Measurement was carried out by using a fully-automatic cell counter TC20.
<Confirmation of Concentration of NRBCs by Cell Sorting>

Figure 13:
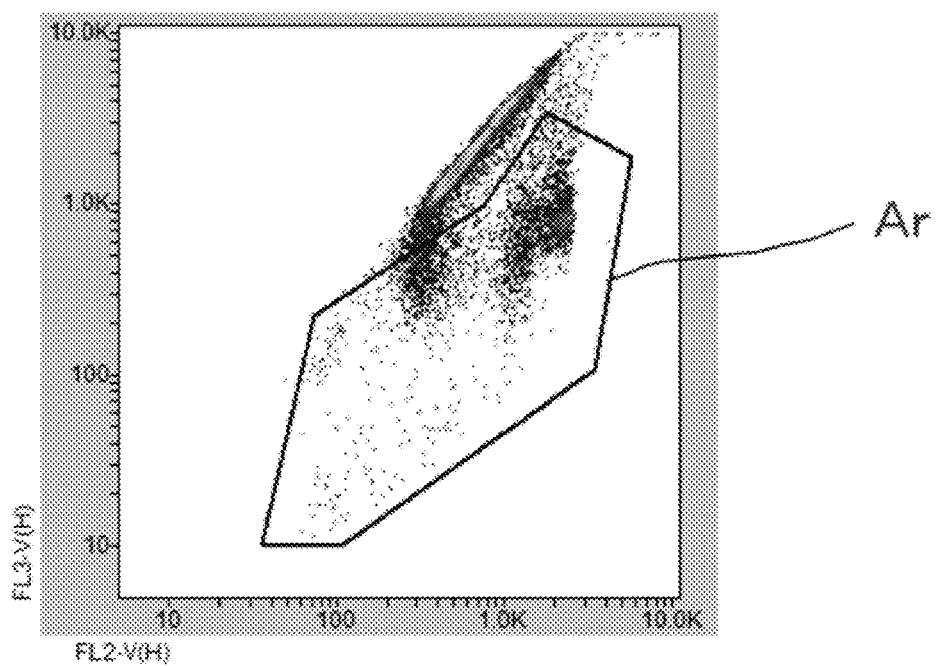
FIG. 13 shows a fluorescence intensity distribution of immunolabeling of Fr2.

One eighth of $3.11 \times 10^7$ blood cells contained in the fraction Fr2 obtained from the maternal blood (i.e., $0.40 \times 10^6$ blood cells) were sorted out by using a cell sorter as in the case of the Example 1. Blood cells that were positive for Hoechst33342 and CD235a and negative for CD45 were sorted out. Through the above-described processes, a fraction containing 15,429 blood cells was obtained (an area Ar in FIG. 13).

By newly separating one eighth of the blood cells from the fraction Fr2 by using the cell sorter, a fraction containing 21,981 blood cells was obtained (an area Ar in FIG. 14).

Chromosomal DNA was extracted from each of the fractions as in the case of the Example 1. Whole genome amplification was performed for the chromosomal DNA by a MALBAC method. After purifying the amplified chromosomal DNA by using NucleoSpin Gel and PCR Clean-up (purchased from Takara Bio Inc.), PCR amplification specific to an SRY gene sequence was performed by using a part of the amplified and purified chromosomal DNA as a template. FIG. 15 shows an electrophoretic image of a PCR product of the SRY gene. Templates are as follows.
[Template]
100 bp DNA ladder is shown on the right side of the lane 5.
Lane 1: distilled water.
Lane 2: Commercially-available standard DNA of Human male, 20 ng.
Lane 3: Commercially-available standard DNA of Human female, 20 ng.
Lane 4: Amplification product of chromosomal DNA contained in maternal blood Fr2 by MALBAC method, 10 ng.
Lane 5: Amplification product of chromosomal DNA contained in maternal blood Fr2 by MALBAC method, 10 ng.
In the PCR using a template of an amplification product of the MALBAC method derived from chromosomal DNA contained in the fraction Fr2 from the maternal blood, an SRY band was observed. No SRY band was observed in the PCR in which other amplification products were used as templates. As described above, it was found that fetal-derived cells can be concentrated by the 60-minute process using the blood cell separation chip.

Further, as shown in the reference example, it is necessary to collect a fraction floating in the centrifuge tube in the density gradient centrifugation method. In contrast to this, in this example using the blood cell separation chip, it was possible to separate a fraction in which fetal-derived cells are concentrated by the blood cell separation chip itself.

Example 3

Figure 16:
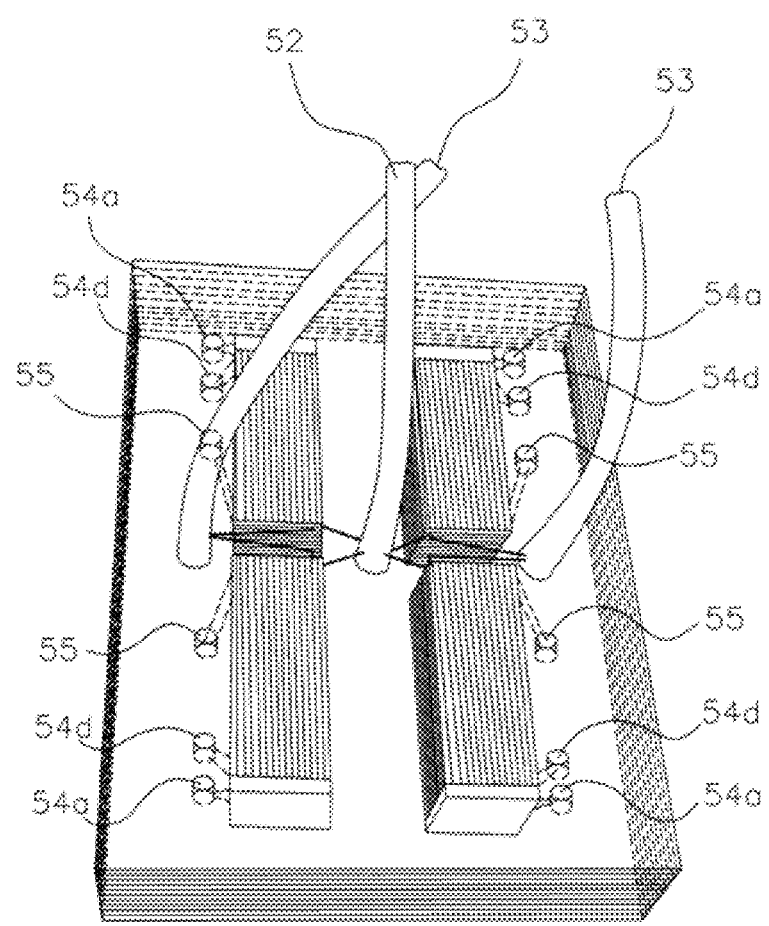
FIG. 16 is a perspective view of a blood-cell separation chip.

The blood cell separation chip used in the Example 2 was modified as shown in FIG. 16 and the modified blood cell separation chip was used. That is, NRBCs were concentrated according to the Example 2 while using the blood cell separation chip having ten layers, wherein four of aforementioned micro-channel units are formed in each of the layer having aforementioned micro-channel unit. Since two or more micro-channel units are formed in each layer, a plurality of vertical micro-channel stacks are formed and arranged in the blood cell separation chip. Pillar channels to which inlets are connected are integrated as a single integrated pillar channel.

The inscribed diameters of the branch channels are the same as those shown in the Example 2. Further, both of the volume of flow per unit time of the diluted maternal blood and that of the PBS to the sub channel in each blood cell separation chip were adjusted to 200 µl per minute. Further, fractionation was performed for 60 minutes by using the blood cell separation chip.

As a result, it was possible to concentrate NRBCs as in the case of the Example 2.

In the above-described embodiments and examples, the present invention has been described by using NRBCs as an example of the target cells. Note that the target cells may not be blood cells. For example, the target cells may be CTCs (Circulating Tumor Cells). In this case, the blood sample may be collected from a subject who needs to take a cancer test, a cancer patient, or a patient who has already been treated for a cancer.

Example 4

<Evaluation of Performance of Multi-layered Chip>

Performance of a multi-layered chip was evaluated as follows. As in the Example 2, whole blood was fractionated by using a multi-layered chip in which layers each of which has a micro-channel unit(s) were successively stacked at regular intervals. The whole blood was that of an ordinary adult who was not pregnant. A dilution of the whole blood was fractionated. The dilution ratio was 5.

The multi-layered chip has the same micro-channel units as those described in the Example 2. However, the multi-layered chip used in this example is different from the multi-layered chip of the Example 2 because the number of layers each of which has a micro-channel unit(s) is eight. Further, a single-layer chip including the same micro-channel unit(s) was used as a control.

The rate of inflow of the diluted blood to the pillar channel to which the inlets of the main channels are collectively connected was adjusted to 20 µl per minute. The diluted blood that has flowed into the multi-layered chip is divided and flows into each of the sub channels in each layer. In the single-layer chip, the rate of inflow of the diluted blood to the only one main channel was adjusted to 20 µl per minute. The volume of blood that was fractionated in each chip was 600 µl.

By making the PBS pass through the sub channel as described above, the PBS restrained the flow of the blood by pressing in the main channel. Irrespective of the number of layers of the chip, the rate of inflow of the PBS to the pillar channel to which the inlets of the sub channels are collectively connected was adjusted to 20 µl per minute (weak pressing) or 40 µl per minute (strong pressing). In the single-layer chip, the rate of inflow of the PBS to the only one sub channel was adjusted to 20 µl per minute. The PBS that has flowed into the multi-layered chip is divided and flows into each of the sub channels in each layer. The volume of the PBS fed into each chip is 600 µl or 1,200 µl.

A fraction F1 was acquired from the branch channel 1 (Fr1, width 15 µm, corresponding to the pillar channel 24a in FIG. 12). A fraction F2 was acquired from the branch channel 2 (Fr2, width 25 µm, corresponding to pillar channel 24d in FIG. 12). A fraction F3 was acquired from the flow-through (Fr3, corresponding to the pillar channel 25 in FIG. 12). Blood cells contained in each of the fractions were analyzed and results are shown in Table 3.

denominator (C3). In the analysis of the fraction F2, the number (C1) of cells collected by the multi-layered chip was used as a denominator. The number (C4) of nucleated cells in each of the fractions was calculated by multiplying the denominator (C3) by the positive ratio (p) (%). Based on the number (C4) of nucleated cells, a distribution ratio of nucleated cells to each of the fractions F1 and F2 was obtained. The distribution ratios of the fractions F1 and F2 are converted so that the sum total of them becomes 100. Further, the ratio of the number (C4) of nucleated cells to the total number of cells collected by the chip is defined as fractionation efficiency (%) and shown in the table.

When the weak pressing (20 µl/min) was applied, the positive ratio (p) of the fraction F2 in the single-layer chip was 4.86%. In contrast to this, the positive ratio (p) in the multi-layered chip was 28.6%. These results indicate that a large number of mature RBCs entered the thick branch channel(s) 2 in the single-layer chip. Further, they indicate that the number of mature RBCs that entered the branch channel(s) 2 was reduced in the multi-layered chip.

When the weak pressing (20 µl/min) was applied, the distribution ratio (F1:F2) of nucleated cells was 42.4:57.6 in the single-layer chip. In contrast to this, the distribution ratio

TABLE 3

| | | | Number of Collected Cells (C1) | Number of Cells after Hemolytic Process (C2) | Population Parameter Used for Calculation of Number of NRBCs (C3) | Positive Ratio in Nuclear Staining (p) (%) | Calculated Number of NRBCs (C4) = (C3) × (p)/100 | Fractionation Efficiency (%) {(C4)/ (C1, Total)} × 100 | Distribution Ratio of NRBCs (F1 + F2 = 100) |
|---|---|---|---|---|---|---|---|---|---|
| Single Layer | Diluted Blood 20 µL/min Pressing 20 µL/min | F1 F2 F3 Total | $1.00 \times 10^9$ $5.58 \times 10^6$ $8.46 \times 10^4$ $1.01 \times 10^9$ | $1.23 \times 10^6$ Not processed — — | (C2) (C1) — — | 16.2 4.86 — — | $1.99 \times 10^5$ $2.71 \times 10^5$ — — | 0.020 0.027 — — | 42.4 57.6 — — |
| | Diluted Blood 20 µL/min Pressing 40 µL/min | F1 F2 F3 Total | $1.06 \times 10^9$ $7.81 \times 10^5$ $9.57 \times 10^4$ $1.06 \times 10^9$ | $1.01 \times 10^6$ Not processed — — | (C2) (C1) — — | 11.7 55.3 — — | $1.18 \times 10^5$ $4.32 \times 10^5$ — — | 0.011 0.041 — — | 21.5 78.5 — — |
| Multi Layers | Diluted Blood 20 µL/min Pressing 20 µL/min | F1 F2 F3 Total | $6.84 \times 10^8$ $1.23 \times 10^6$ $3.82 \times 10^4$ $6.85 \times 10^8$ | $4.22 \times 10^5$ Not processed — — | (C2) (C1) — — | 7.09 28.6 — — | $2.99 \times 10^4$ $3.50 \times 10^5$ — — | 0.004 0.051 — — | 7.9 92.1 — — |
| | Diluted Blood 20 µL/min Pressing 40 µL/min | F1 F2 F3 Total | $8.27 \times 10^8$ $5.01 \times 10^4$ $2.79 \times 10^4$ $8.27 \times 10^8$ | $1.96 \times 10^5$ Not processed — — | (C2) (C1) — — | 8.22 66.6 — — | $1.61 \times 10^4$ $3.34 \times 10^4$ — — | 0.002 0.040 — — | 4.6 95.4 — — |

The analyses are explained. The number (C1) of cells collected into each of the fractions F1 to F3 was measured by using a fully-automatic cell counter TC20 (BIORAD). It should be noted that the fraction F1 was first diluted to 400 times and then the number of cells was measured. This is because the fraction F1 contains a large number of cells, mainly enucleated mature RBCs. The dilution ratio may be 100 to 200.

A hemolytic process is performed for the fraction F1. As a result, the mature RBCs in the fraction F1 are hemolyzed. Nucleated cells including WBCs remain even after the hemolysis. Some of the remaining cells were analyzed by the FCM. Regarding the fraction F2, some of the collected cells were analyzed by the FCM. Fluorescent nuclear staining was performed for the hemolyzed fraction F1 and for the fraction F2. The positive ratio (p) (%) in the nuclear staining was measured by the FCM.

In the analysis of the fraction F1, the number (C2) of remaining cells after the hemolytic process was used as a was 7.9:92.1 in the multi-layered chip. These results indicate that a large number of nucleated cells entered the narrow branch channel(s) 1 in the single-layer chip. Further, they indicate that the number of nucleated cells that entered the branch channel(s) 1 was reduced in the multi-layered chip.

Based on the above-described results, it has been found that the accuracy for the hydraulic classification for mature RBCs and nucleated cells is higher in the multi-layer chip than in the single-layer chip.

Further, fractionation with the strong pressing (40 µl/min) was carried out in order to improve the accuracy for the classification. The positive ratio (p) of the fraction F2 was improved to 55.3% in the single-layer chip. It was improved to 66.6% even in the multi-layered chip. These results indicate that the number of mature RBCs that entered the branch channel(s) 2 was reduced by making the pressing and restraining stronger.

When the strong pressing (40 µl/min) was applied, the distribution ratio (F1:F2) of nucleated cells was 21.5:78:5 in the single-layer Chip. It was 4.6:95.4 even in the multi-layered chip. These results indicate that the accuracy for the classification can be improved by making the pressing and restraining stronger.

The improvement in the distribution ratio that was achieved by applying the strong pressing (40 µl/min) was very large in the single-layer chip. However, the distribution ratio was not significantly improved in the multi-layered chip. It is considered that this is because the distribution ratio was already sufficiently shifted toward the fraction F2 side even when the pressing was weak (20 µl/min). As described above, it has been found that the multi-layered structure of the chip provides means capable of improving the accuracy for the classification irrespective of the strength of the pressing and restraining.

This application is based upon and claims the benefit of priority from Japanese patent application FIG. 2017-202907, filed on Oct. 19, 2017, the disclosure of which is incorporated herein in its entirety by reference.

Other aspects of the present invention are described hereinafter.

[1] A method for acquiring a fraction in which nucleated red blood cells (NRBCs) are concentrated in a population of whole blood cells by fractionating blood cells contained in a blood sample by using a blood cell separation chip, in which the blood sample is a non-treated blood sample itself or an un-filtered/un-concentrated sample in which NRBCs are not concentrated in the population of whole blood cells as compared to the blood sample, the blood cell separation chip includes a micro-channel unit including a main channel through which the blood sample flows, a sub channel connected to a side of the main channel, a removal channel connected, downstream from the sub channel, to a side of the main channel opposite to the side thereof to which the sub channel is connected, and a collection channel connected, downstream from the removal channel, to the side of the main channel opposite to the side thereof to which the sub channel is connected, liquid flowing from the sub channel pushes blood cells flowing in the main channel toward the side thereof on which the removal channel and the collection channel are disposed, non-nucleated RBCs among the pushed blood cells enter the removal channel, so that the non-nucleated RBCs are removed from the blood sample, among the remaining blood cells from which the non-nucleated RBCs have been removed, NRBCs enter the collection channel, so that the NRBCs are acquired as the fraction from the blood sample, and the removal channel and the collection channel have different inscribed diameters, and the inscribed diameter of the removal channel at a connecting part between the main channel and the removal channel is smaller than that of the collection channel at a connecting part between the main channel and the collection channel.

[2] The method described in the Item [1], in which the blood sample is a maternal blood sample and the NRBCs are fetal-derived NRBCs.

[3] The method described in the Item [1], in which the inscribed diameter of the removal channel at the connecting part between the main channel and the removal channel is 4 to 19 µm, and the inscribed diameter of the collection channel at the connecting part between the main channel and the collection channel is 20 to 30 µm.

[4] The method described in the Item [1], in which a volume of flow per minute of the blood sample to the main channel is 0.5 to 50 µl.

[5] The method described in the Item [1], in which a volume of flow per minute of the blood sample to the sub channel is 1 to 10 times the volume of flow to the main channel.

[6] The method described in the Item [1], in which all channels are two-dimensionally arranged in the micro-channel unit, and the separation chip includes 2 to 200 layers each of which includes the micro-channel unit, the micro-channel units provided in the respective layers are put on top of each other in a vertical direction and thereby form a micro-channel stack, and in layered channels, injection ports of main channels, injection ports of sub channels, discharging ports of removal channels, discharging ports of collection channels, and discharging ports of the main channels provided in the micro-channel units in the respective layers are connected to respective vertical channels penetrating all the layers so that they are separately put together.

[7] The method described in the Item [6], in which the injection port of the main channel in the bottom layer is closed and the discharging port of the main channel in an uppermost layer or a lowermost layer is closed.

[8] The method described in the Item [6], in which at least two micro-channel units are formed in each layer including the micro-channel units, and hence a plurality of vertical micro-channel stacks are formed and arranged in the blood cell separation chip, and the vertical channels to which the injection ports are connected are integrated as a single integrated vertical channel.

[9] The method described in the Item [1], in which the blood sample is periodically stirred while the blood sample is being injected.

[10] The method described in the Item [1], in which in the micro-channel unit, the inscribed diameter of the collection channel is increased in an intermediate part of the collection channel, and the inscribed diameter of the removal channel is increased in an intermediate part of the removal channel.

[11] A method for acquiring data used for a diagnosis in noninvasive prenatal genetic testing, including:

acquiring a fraction A in which NRBCs are concentrated in a population of whole blood cells by fractionating blood cells contained in a blood sample by using a blood cell separation chip, in which the blood sample is a non-treated blood sample itself or an un-filtered/un-concentrated sample in which NRBCs are not concentrated in the population of whole blood cells as compared to the blood sample;

acquiring a fraction B by specifically labeling white blood cells (WBCs) and nucleic acids in the fraction A and sorting out labeled blood cells in the fraction A by cell sorting, in which blood cells labeled with a label specific to the WBCs have been removed from the fraction B and blood cells labeled with a label specific to the nucleic acids have been concentrated in the fraction B; and acquiring data to be used for a diagnosis in noninvasive prenatal genetic testing by analyzing a chromosome contained in the blood cells in the fraction B, in which the blood cell separation chip includes a micro-channel unit including a main channel through which the blood sample flows, a sub channel connected to a side of the main channel, a removal channel connected, downstream from the sub channel, to a side of the main channel opposite to the side thereof to which the sub channel is connected, and a collection channel connected, downstream from the removal channel, to the side of the main channel opposite to the side thereof to which the sub channel is connected, liquid flowing from the sub channel pushes blood cells flowing in the main channel toward the side thereof on which the removal channel and the collection channel are disposed, non-nucleated RBCs among the pushed blood cells enter the removal channel, so that the non-nucleated RBCs are removed from the blood sample, among the remaining blood cells from which the non-nucleated RBCs have been removed, NRBCs enter the collection channel, so that the NRBCs are acquired as the fraction from the blood sample, and the removal channel and the collection channel have different inscribed diameters, and the inscribed diameter of the removal channel at a connecting part between the main channel and the removal channel is smaller than that of the collection channel at a connecting part between the main channel and the collection channel.

[12] The method described in the Item [11], in which the analysis of the chromosome is an analysis according to a fluorescence in situ hybridization method, a next generation genome sequencing method, or a microarray method.

[13] The method described in the Item [11], in which the blood sample is a maternal blood sample and the NRBCs are fetal-derived NRBCs.

[14] The method described in the Item [11], in which the inscribed diameter of the removal channel at the connecting part between the main channel and the removal channel is 4 to 19 µm, and the inscribed diameter of the collection channel at the connecting part between the main channel and the collection channel is 20 to 30 µm.

[15] The method described in the Item [11], in which a volume of flow per minute of the blood sample to the main channel is 0.5 to 50 µl.

[16] The method described in the Item [11], in which a volume of flow per minute of the blood sample to the sub channel is 1 to 10 times the volume of flow to the main channel.

[17] The method described in the Item [11], in which all channels are two-dimensionally arranged in the micro-channel unit, and the separation chip includes 2 to 200 layers each of which includes the micro-channel unit, the micro-channel units provided in the respective layers are put on top of each other in a vertical direction and thereby form a micro-channel stack, and in layered channels, injection ports of main channels, injection ports of sub channels, discharging ports of removal channels, discharging ports of collection channels, and discharging ports of the main channels provided in the micro-channel units in the respective layers are connected to respective vertical channels penetrating all the layers so that they are separately put together.

[18] The method described in the Item [17], in which the injection port of the main channel in the bottom layer is closed and the discharging port of the main channel in an uppermost layer or a lowermost layer is closed.

[19] The method described in the Item [17], in which at least two micro-channel units are formed in each layer including the micro-channel units, and hence a plurality of vertical micro-channel stacks are formed and arranged in the blood cell separation chip, and the vertical channels to which the injection ports are connected are integrated as a single integrated vertical channel.

[20] The method described in the Item [11], in which the blood sample is periodically stirred while the blood sample is being injected.

[21] The method described in the Item [11], in which in the micro-channel unit, the inscribed diameter of the collection channel is increased in an intermediate part of the collection channel, and the inscribed diameter of the removal channel is increased in an intermediate part of the removal channel.

REFERENCE SIGNS LIST

20 CHIP
22 PILLAR CHANNEL TO WHICH INLETS OF MAIN CHANNELS ARE COLLECTIVELY CONNECTED
23 PILLAR CHANNEL TO WHICH INLETS OF SUB CHANNELS ARE COLLECTIVELY CONNECTED
24a PILLAR CHANNEL TO WHICH OUTLETS OF REMOVAL CHANNELS ARE COLLECTIVELY CONNECTED
24d PILLAR CHANNEL TO WHICH OUTLETS OF COLLECTION CHANNELS ARE COLLECTIVELY CONNECTED
25 PILLAR CHANNEL TO WHICH OUTLETS OF MAIN CHANNELS ARE COLLECTIVELY CONNECTED
39 GRANULE
41 NUCLEATED RED BLOOD CELLS (NRBCs)
42 NON-NUCLEATED RED BLOOD CELLS (NON-NUCLEATED RBCs)
43 WHITE BLOOD CELLS (WBCs)
45a-45f LAYERS
46 CENTRIFUGE TUBE
47 MAIN CHANNEL
48a-48c BLOOD CELL
49 SUB CHANNEL
50 BLOOD-CELL SEPARATION CHIP
51 INLET
52 MAIN CHANNEL
53 SUB CHANNEL
54a-54d OUTLET
55 OUTLET
56a-56d CHANNEL
57 SYRINGE
58 SYRINGE
59a-59d BRANCH CHANNEL
62 INLET
Fr1-Fr5 FRACTION
FT FLOW-THROUGH
L01-L10 LAYER

The invention claimed is:

1. A chip, comprising:

a micro-channel unit for hydraulically classifying cells in a blood sample, the micro-channel unit comprising a pattern in which a main channel through which the blood sample flows, a sub channel connected to a side of the main channel, removal channels connected, downstream from the sub channel, to a side of the main channel opposite to the side thereof to which the sub channel is connected, and collection channels connected, downstream from the removal channel, to the side of the main channel opposite to the side thereof to which the sub channel is connected are two-dimensionally extended, liquid flowing from the sub channel into the main channel pushes cells flowing in the main channel toward the side thereof on which the removal channels and the collection channels are disposed, fluid containing non-nucleated red blood cells among the pushed cells enters the removal channels, so that the non-nucleated red blood cells are removed from the blood sample, fluid containing target cells among the remaining cells from which the non-nucleated red blood cells have been removed enters the collection channels, so that the target cells are acquired from the blood sample, a volume of flow per unit time, in each collection channel, on a cross section of a connecting part between the main channel and that collection channel is larger than a volume of flow per unit time, in each removal channel, on a cross section of a connecting part between the main channel and that removal channel, a plurality of micro-channel units having the same patterns as each other are repeatedly stacked in a height direction by stacking layers in which at least one micro-channel unit is provided, and inlets of the main channels, inlets of the sub channels, outlets of the removal channels, outlets of the collection channels, and outlets of the main channels, which are provided in the micro-channel units, are connected to respective pillar channels penetrating each layer in a traversing manner so that they are separately put together by the respective pillar channels.

2. The chip according to claim 1, wherein one micro-channel unit is provided in each of the layers.

3. The chip according to claim 2, wherein orientations and positions of the patterns of the micro-channel units of all the layers are aligned with each other in a planer view of the chip.

4. The chip according to claim 3, wherein
the pillar channels to which the inlets of the main channels and the sub channels are respectively connected have openings on a top surface of the chip, and
the pillar channels to which the outlets of the removal channels and the collection channels are respectively connected have openings on a bottom surface of the chip,
so that the blood sample passes through the chip from the top surface of the chip to the bottom surface thereof.

5. The chip according to claim 4, wherein the layers, in which the micro-channel units are provided, are successively stacked at regular intervals.

6. The chip according to claim 1, wherein
an inscribed diameter of the removal channel at the connecting part between the main channel and the removal channel is 4 to 19 μm, and
an inscribed diameter of the collection channel at the connecting part between the main channel and the collection channel is 20 to 30 μm.

7. The chip according to claim 1, wherein in the micro-channel unit, a cross-sectional area the collection channel becomes larger toward downstream of the collection channel, or a cross-sectional area of the removal channel becomes larger toward downstream of the removal channel.

8. A method of using a chip comprising a micro-channel unit for hydraulically classifying cells in a blood sample,
the micro-channel unit comprising a pattern in which a main channel through which the blood sample flows, a sub channel connected to a side of the main channel, removal channels connected, downstream from the sub channel, to a side of the main channel opposite to the side thereof to which the sub channel is connected, and collection channels connected, downstream from the removal channel, to the side of the main channel opposite to the side thereof to which the sub channel is connected are two-dimensionally extended, liquid flowing from the sub channel into the main channel pushes cells flowing in the main channel toward the side thereof on which the removal channels and the collection channels are disposed, fluid containing non-nucleated red blood cells among the pushed cells enters the removal channels, so that the non-nucleated red blood cells are removed from the blood sample, fluid containing target cells among the remaining cells from which the non-nucleated red blood cells have been removed enters the collection channels, so that the target cells are acquired from the blood sample, a volume of flow per unit time, in each collection channel, on a cross section of a connecting part between the main channel and that collection channel is larger than a volume of flow per unit time, in each removal channel, on a cross section of a connecting part between the main channel and that removal channel, a plurality of micro-channel units having the same patterns as each other are repeatedly stacked in a height direction by stacking layers in which at least one micro-channel unit is provided, and inlets of the main channels, inlets of the sub channels, outlets of the removal channels, outlets of the collection channels, and outlets of the main channels, which are provided in the micro-channel units, are connected to respective pillar channels penetrating each layer in a traversing manner so that they are separately put together by the respective pillar channels, wherein the chip is used for acquiring a fraction in which the target cells are concentrated in terms of the number of cells by fractionating the blood sample, wherein
the blood sample is non-treated whole blood itself or one in which the target cells are not concentrated in terms of the number of cells as compared to the whole blood.

9. The method of using the chip according to claim 8, wherein a volume of inflow of the blood sample to the pillar channel to which the main channel is connected is 8 to 25 μl/min.

10. The method of using the chip according to claim 9, wherein a volume of inflow per unit time of the liquid to the pillar channel to which the sub channel is connected is 1 to 2 times a volume of inflow per unit time of the blood sample to the pillar channel to which the main channel is connected.

11. The method of using the chip according to claim 8, wherein while the blood sample is being injected into the chip, the blood sample that is held before being injected into the chip is stirred, and the stirred blood sample is successively injected into the chip.

12. The method of using the chip according to claim 8, wherein
the blood sample is whole blood of maternal blood or one that is obtained by simply diluting the whole blood, and
the target cells are fetal-derived nucleated red blood cells.

13. A method comprising:
acquiring a fraction A in which nucleated red blood cells are concentrated based on a use of the chip according to claim 12:
acquiring a fraction B by specifically labeling white blood cells and nucleic acids in the fraction A and sorting out labeled blood cells in the fraction A by cell sorting, in which blood cells labeled with a label specific to the white blood cells have been removed from the fraction B and blood cells labeled with a label specific to the nucleic acids have been concentrated in the fraction B; and acquiring data to be used for a diagnosis in noninvasive prenatal genetic testing by analyzing a chromosome contained in the blood cells in the fraction B.

14. The method according to claim 13, wherein the analysis of the chromosome is an analysis according to a fluorescence in situ hybridization method, a next generation sequencing method, or a microarray method.

* * * * *